United States Patent [19]

Tseng et al.

US005696093A

[11] Patent Number: 5,696,093
[45] Date of Patent: Dec. 9, 1997

[54] METHOD OF TREATING NASAL CONGESTION USING NEUROPEPTIDE Y Y2 AGONIST PEPTIDES

[75] Inventors: Albert Tseng, Epping, Australia; Lisa Selbie, Ashbourne, United Kingdom; Erica Potter, Randwick, Australia

[73] Assignee: CRC for Biopharmaceutical Research Pty Limited, Darlinghurst, Australia

[21] Appl. No.: 330,727

[22] Filed: Oct. 28, 1994

[51] Int. Cl.$^6$ .................... C07K 14/00; A61K 38/00
[52] U.S. Cl. ...................... 514/14; 514/12; 514/13
[58] Field of Search ........................ 514/14, 12, 13

[56] References Cited

U.S. PATENT DOCUMENTS

| | | | |
|---|---|---|---|
| 4,701,441 | 10/1987 | Kalra | 514/12 |
| 5,026,685 | 6/1991 | Boublik et al. | 514/13 |
| 5,395,823 | 3/1995 | Kirstenansky | 514/12 |

FOREIGN PATENT DOCUMENTS

| | | |
|---|---|---|
| 3811193 | 10/1989 | Germany . |
| 9400486 | 1/1994 | WIPO . |

*Primary Examiner*—Robert J. Hill, Jr.
*Assistant Examiner*—P. Lynn Touzeau
*Attorney, Agent, or Firm*—Rothwell, Figg, Ernst & Kurz

[57] ABSTRACT

The invention relates to neuropeptide Y-$Y_2$ receptor specific peptides. Preferred peptides areas follows:

$CH_3CO$—Leu—Arg—His—Tyr—Leu—Asn—Leu—Leu—Thr—Arg—Gln—Arg—Tyr—$NH_2$, or $CH_3CO$—Leu—Arg—His—Tyr—Ile—Asn—Leu—Ile—Thr—Arg—Gln—Arg—Tyr—$NH_2$, or $NH_2$—Leu—Arg—His—Tyr—Leu—Asn—Leu—Leu—Thr—Arg—Gln—Arg—Tyr—$NH_2$, or $NH_2$—Leu—Arg—His—Tyr—Ile—Asn—Leu—Ile—Thr—Arg—Gln—Arg—Tyr—$NH_2$.

The peptides are preferably used in relieving nasal congestion.

4 Claims, 10 Drawing Sheets

METHOD OF TREATING NASAL CONGESTION USING NEUROPEPTIDE Y Y2 AGONIST PEPTIDES

Neuropeptide Y, a 36 amino acid peptide belonging to the pancreatic polypeptide family, was first isolated from porcine brain in 1982 (Tatemoto et al., 1982) and has since been identified in most sympathetic postganglionic neurons innervating the cardiovascular system, where it is co-localised with noradrenaline (Potter, 1988). In the cardiovacsular system it raises blood pressure by an action on postjunctional neuropeptide Y receptors (Dahlöff et al., 1985; Potter, 1985; Revington et al., 1987; Potter and McCloskey, 1992) and inhibits neurotransmitter release—both acetylcholine (Revington et al., 1987; Warner and Levy, 1989) and noradrenaline (Edvinsson, 1988)—by acting on prejunctional neuropeptide Y $Y_2$ (postjunctional) and neuropeptide Y $Y_1$ (prejunctional) on the basis of the different responses to a truncated analog of the related peptide YY-(13-36), when compared with neuropeptide Y in in vitro assay systems (Wahlestedt et al., 1986). Although some controversy has existed about the selectivity of truncated forms of neuropeptide Y for one or other receptor subtype (Potter et al., 1989), the emerging picture supports the initial classification into pre- and postjunctional receptor subtypes. Cell lines have been developed which express one or other neuropeptide Y receptor subtype and the development of receptor-selective analogs of neuropeptide Y has focussed mainly on binding characteristics in these cell lines (Sheikh et al., 1988; Aakerlund et al., 1990; Fuhlendorff et al., 1990). More recently, a cDNA encoding the neuropeptide Y $Y_1$ receptor has been cloned and cell lines expressing the cloned receptor have been analysed for both specific binding of neuropeptide Y analogs (Herzog et al., 1992) and functional responses elicited by specific analogs. From such binding studies, combined with subsequent studies in vivo, two analogs have been classified as acting specifically on the postjunctional (neuropeptide Y $Y_1$) receptor. These neuropeptide Y $Y_1$ selective analogs, [Pro$^{34}$] neuropeptide Y and [Leu$^{31}$, Pro$^{34}$] neuropeptide Y, mimic the action of neuropeptide Y in raising blood pressure, and also share similar binding to cell lines expressing only neuropeptide Y $Y_1$ receptors e.g. rat phaceochromocytoma cell line PCl2, the human neuroblastoma cell line SK-N-MC and fibroblast lines expressing the cloned neuropeptide Y $Y_1$ (Herzog et al 1992). Neither exhibits the neuropeptide Y $Y_2$-receptor action of inhibiting cardiac vagal action in vivo, a manifestation of inhibition of acetylcholine release (Potter et al., 1991, Potter and McCloskey, 1992).

The prejunctional or neuropeptide Y $Y_2$ receptor classification was based on actions of peptide YY (13-36) but in many systems this molecule, as well as neuropeptide Y-(13-36), does exhibit pressor activity (Rioux et al., 1986; Lundberg, et al., 1988., Potter et al., 1989). This has been interpreted by some to indicate that in some vascular beds there are two types of neuropeptide Y receptor (both neuropeptide Y $Y_1$ and neuropeptide Y $Y_2$) on postjunctional membranes (Schwartz et al., 1989). However the lack of selectivity of these molecules may be due to retention of partial agonist activity on $Y_1$ receptors, which permits them to evoke a reduced but still functional response. We have previously described a 13-36 analog of neuropeptide Y, [Leu$^{17}$, Glu$^{19}$, Ala$^{21}$, Ala$^{22}$, Glu$^{23}$, Leu$^{28}$, Leu$^{31}$], neuropeptide Y-(13-36) (ANA neuropeptide Y-(13-36)) which displayed prejunctional activity equivalent to the whole neuropeptide Y molecule in studies in vivo (Potter et al., 1989). However, this analog still retained significant pressor activity, or neuropeptide Y $Y_1$ receptor-mediated interactions.

The present inventors have developed new analogs of neuropeptide Y which mimic the action of neuropeptide Y in inhibiting cardiac vagal action but have no pressor action. Consistent with these functional responses are binding studies with one analog, N-acetyl [Leu$^{28}$, Leu$^{31}$] neuropeptide Y-(24-36), which shows significant affinity for the neuropeptide Y $Y_2$ receptor subtype expressed on the human neuroblastoma cell line SMS-KAN, but no affinity for the neuropeptide Y $Y_1$ receptor type expressed on the human cell line SK-N-MC. In addition, this analog does not stimulate the human neuropeptide Y $Y_1$ receptor expressed in fibroblast cells to induce an increase in cytosolic calcium, although the receptor responds to intact neuropeptide Y.

Accordingly, in the first aspect of the present invention consists in a neuropeptide Y Y2 receptor specific peptide, the peptide having the formula:

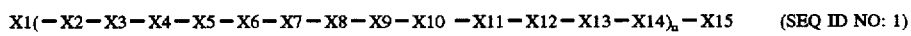

X1(—X2—X3—X4—X5—X6—X7—X8—X9—X10—X11—X12—X13—X14)$_n$—X15     (SEQ ID NO: 1)

wherein

X1 is NH, CH$_3$CO or one or two naturally occurring amino acids

X2 is Leu, Ile or Val.

X3 is Arg, Lys or His.

X4 is His, Lys or Arg.

X5 is Tyr or Phe.

X6 is Leu, Ile or Val.

X7 is Asn or Gln.

X8 is Leu, Ile or Val.

X9 is Leu, Ile or Val.

X10 is Thr or Ser.

X11 is Arg, His or Lys.

X12 is Gln or Asn.

X13 is Arg, His or Lys.

X14 is Tyr or Phe.

X15 is COOH, NH$_2$ or one or two naturally occurring amino acids with the terminal amino acid being in the normal or carboxamide form; and n is 1 to 5.

In the preferred embodiment of the present invention the peptide is

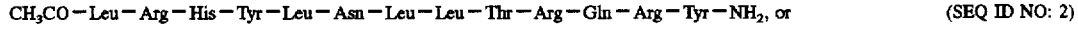

CH$_3$CO—Leu—Arg—His—Tyr—Leu—Asn—Leu—Leu—Thr—Arg—Gln—Arg—Tyr—NH$_2$, or     (SEQ ID NO: 2)

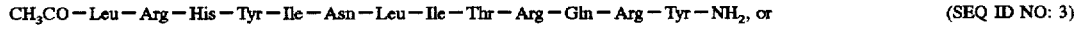

CH$_3$CO—Leu—Arg—His—Tyr—Ile—Asn—Leu—Ile—Thr—Arg—Gln—Arg—Tyr—NH$_2$, or     (SEQ ID NO: 3)

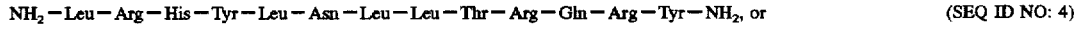

NH$_2$—Leu—Arg—His—Tyr—Leu—Asn—Leu—Leu—Thr—Arg—Gln—Arg—Tyr—NH$_2$, or     (SEQ ID NO: 4)

-continued

NH$_2$—Leu—Arg—His—Tyr—Ile—Asn—Leu—Ile—Thr—Arg—Gln—Arg—Tyr—NH$_2$, and is most preferably (SEQ ID NO: 5)

CH$_3$CO—Leu—Arg—His—Tyr—Leu—Asn—Leu—Leu—Thr—Arg—Gln—Arg—Tyr—NH$_2$. (SEQ ID NO: 2)

In the second aspect the present invention consists in a composition for use in relieving nasal congestion, antihypertensive therapy, cardiovascular therapy, anti-obesity and anti-diabetic therapy or as an anti-psychotic, the composition comprising the peptide of the first aspect of the present invention and a pharmaceutical carrier.

In a third aspect the present invention consists in a method of relieving nasal congestion, treating hypertension, attenuating cardiac vagal action, obesity, diabetes or Alzheimers disease in a subject comprising administering to the subject an effective amount of the composition of the second aspect of the present invention.

In a preferred embodiment of the third aspect of the present invention the subject is suffering from nasal congestion. In a further preferred embodiment the composition is administered as a nasal spray.

It will be appreciated by those skilled in the art that a number of modifications may be made to the peptides of the present invention without deleteriously affecting the biological activity of the peptide. This may be achieved by various changes, such as insertions, deletions and substitutions either conservative or non-conservative in the peptide sequence where such changes do not substantially decrease the biological activity of the peptide.

It may also be possible to add various groups to the peptide of the present invention to confer advantages such as increased potency or extended half life in-vivo without substantially decreasing the biological activity of the peptide. It is intended that such modifications to the peptide of the present invention which do not result in a decrease in biological activity are within the scope of the present invention.

BRIEF DESCRIPTION OF THE DRAWINGS

In order that the nature of the present invention may be more clearly understood, preferred forms thereof will now be described with reference to the following examples and Figures in which.

(A) Increasing concentrations of porcine PYY (■), neuropeptide Y (○), [Leu$^{28}$, Leu$^{31}$] neuropeptide Y-(24-36) (△), N-acetyl [Leu$^{28}$, Leu$^{31}$] neuropeptide Y-(24-36) (□), and neuropeptide Y-(13-32) (▲) were tested for their ability to inhibit the binding of specifically bound radiolabelled PYY to human neuroblastoma SMS-KAN cells (which express an endogenous Y$_2$-like neuropeptide Y receptor). A representative experiment of at least three determinations is shown. Standard errors of triplicate samples are shown.

(B) Increasing concentrations of porcine PYY (■), neuropeptide Y (○), [Leu$^{17}$, Gln$^{19}$, Ala$^{21}$, Ala$^{22}$, Glu$^{23}$, Leu$^{28}$, Leu$^{31}$] neuropeptide Y-(13-36) (●), [Leu$^{28}$, Leu$^{31}$] neuropeptide Y-(24-36) (△) and N-acetyl [Leu$^{28}$, Leu$^{31}$] neuropeptide Y-(24-36) (□) were tested for their ability to inhibit the binding of specifically bound radiolabelled PYY to human neuroblastoma SK-N-MC cells (which express an endogenous Y$_1$-like receptor). The experiment was performed twice. Standard errors of triplicate samples are shown.

FIG. 3. Neuropeptide Y Y$_1$ receptor-mediated increases in intracellulase cytosolic calcium levels.

CHO cells transfected with the cloned human neuropeptide Y Y$_1$ receptor and loaded with calcium-sensitive fluorescent dye Fura-2 AM were incubated with 1 µM of peptide YY (P) (panel A), or N-acetyl [Leu$^{28}$, Leu$^{31}$] neuropeptide Y-(24-36) (Ac) (Panel B). Following each addition, the endogenous ATP receptor was stimulated with 1 µM ATP (A). The increase in calcium concentration (nM) was calculated as described. The results of this figure show the calcium response to 1 µM peptide YY was 39.4 nM (n=2; panel A) before the addition of N-acetyl [Leu$^{28}$, Leu$^{31}$] neuropeptide Y-(24-26) and 39.6 nM (n=2; panel B) after the addition. The calcium response to 1 µM ATP before addition of N-acetyl [Leu$^{28}$, Leu$^{31}$] neuropeptide Y-(24-36) was 46.3 nM (n=2) and after addition was 33.8 nM. The experiments were done in duplicate and a representative result is shown.

Figure 4:
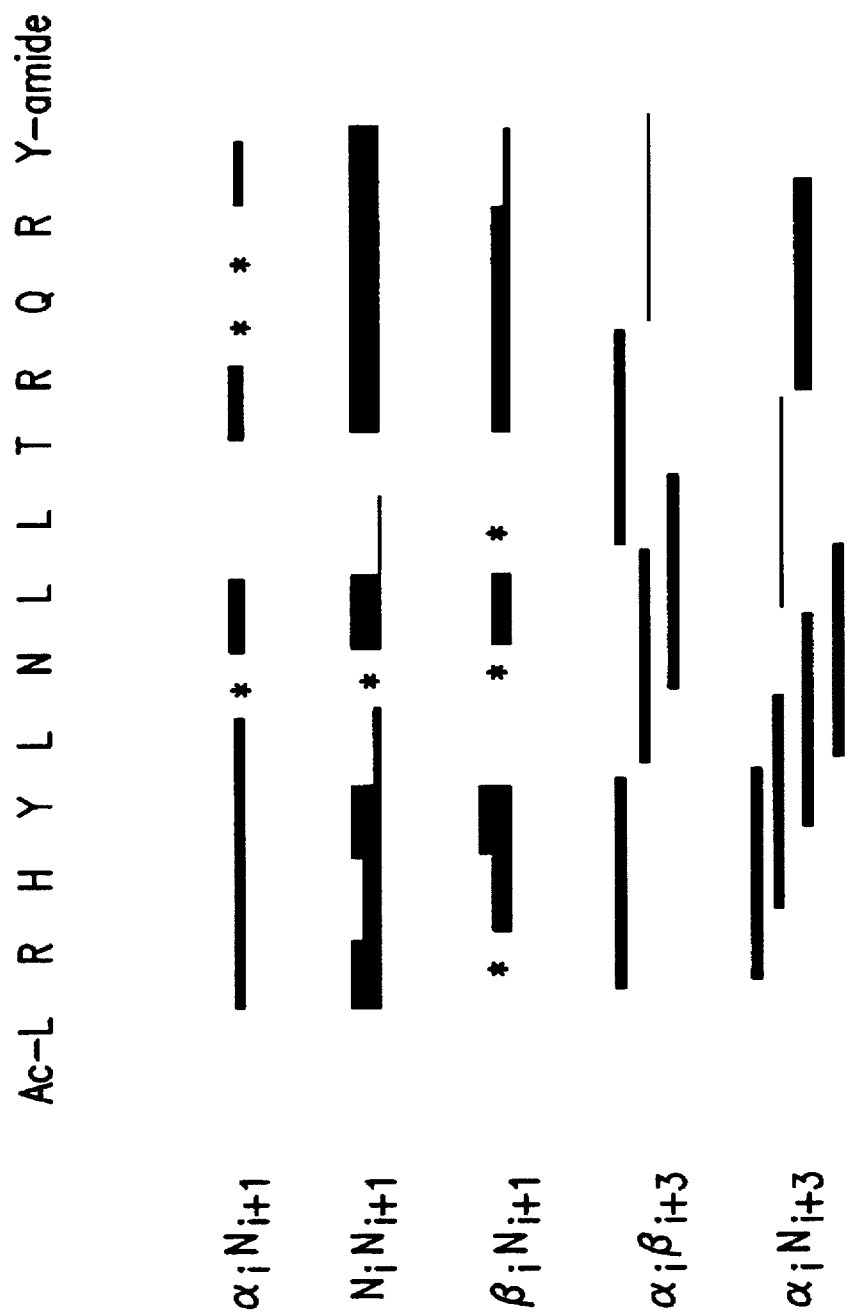

FIG. 4. Summary of short- and medium-range inter-residue NOE connectivities observed for N-acetyl [Leu$^{28}$, Leu$^{31}$] neuropeptide Y-(24-36) reflecting the presence of regular secondary structure. The solid bars show the presence of an NOE with the thickness being proportional to the intensity of the NOE. The thickest bar refers to an upper distance limit of 0.3 nm while the thinnest bar refers to a limit of 0.45 nm. An overlapped NH resonance is represented by an asterix. Medium range NOEs $\alpha_{i\beta i+3}$ from 2–5, 3–6, and 7–10 and $\alpha_i N_{i+3}$ from, 5–8, 7–10 were also overlapped.

FIG. 5 Recording from an anaesthetised dog showing changes in blood flow in the internal maxillary artery upon stimulation of the parasympathetic nerve (PS, 5 V, 5 m) at 30 Hz for 10 sec. during sympathetic nerve stimulation (SNS, 15 V, 5 ms, for 3 min) and the effect of subsequent parasympathetic stimulations. Note that one hour later, the effect of the parasympathetic stimulation is of the same magnitude as that before sympathetic nerve stimulation. (a) under control conditions, (b) after pretreatment with phentolamine (0.5 mg/kg/h), propranolol (1 mg/kg) and atropine (0.5 mg/kg). In panel (c) the vasoconstrictor effect of exogenous NPY (8 nmol kg$^{-1}$, i.v.) is similar to the sympathetic stimulation shown in (b) as well as the inhibition of the subsequent parasympathetic vasodilatation. Time scale is given by the PS stimulation for 10 sec.

FIG. 6 Effects of parasympathetic nerve stimulation (5 V, 5 ms) at different frequencies on the vascular resistance in the internal maxillary artery ($R_{ma}$) of the dog (a) under control conditions (open bar) and (b) after pretreatment with phentolamine (0.5 mg/kg/h), propanolol (1 mg/kg) and atropine (0.5 mg/kg) (horizontal hatched bar). The effects of the same parasympathetic stimulations are also shown just after sympathetic nerve stimulation (15 V, 5 ms, 10 Hz, 3 min) (diagonal hatched bar), 30 min after sympathetic stimulation (cross hatched bar) and one hour later (filled bar). n=8, p<0.05 when compared to control (one way ANOVA test).

Figure 7:
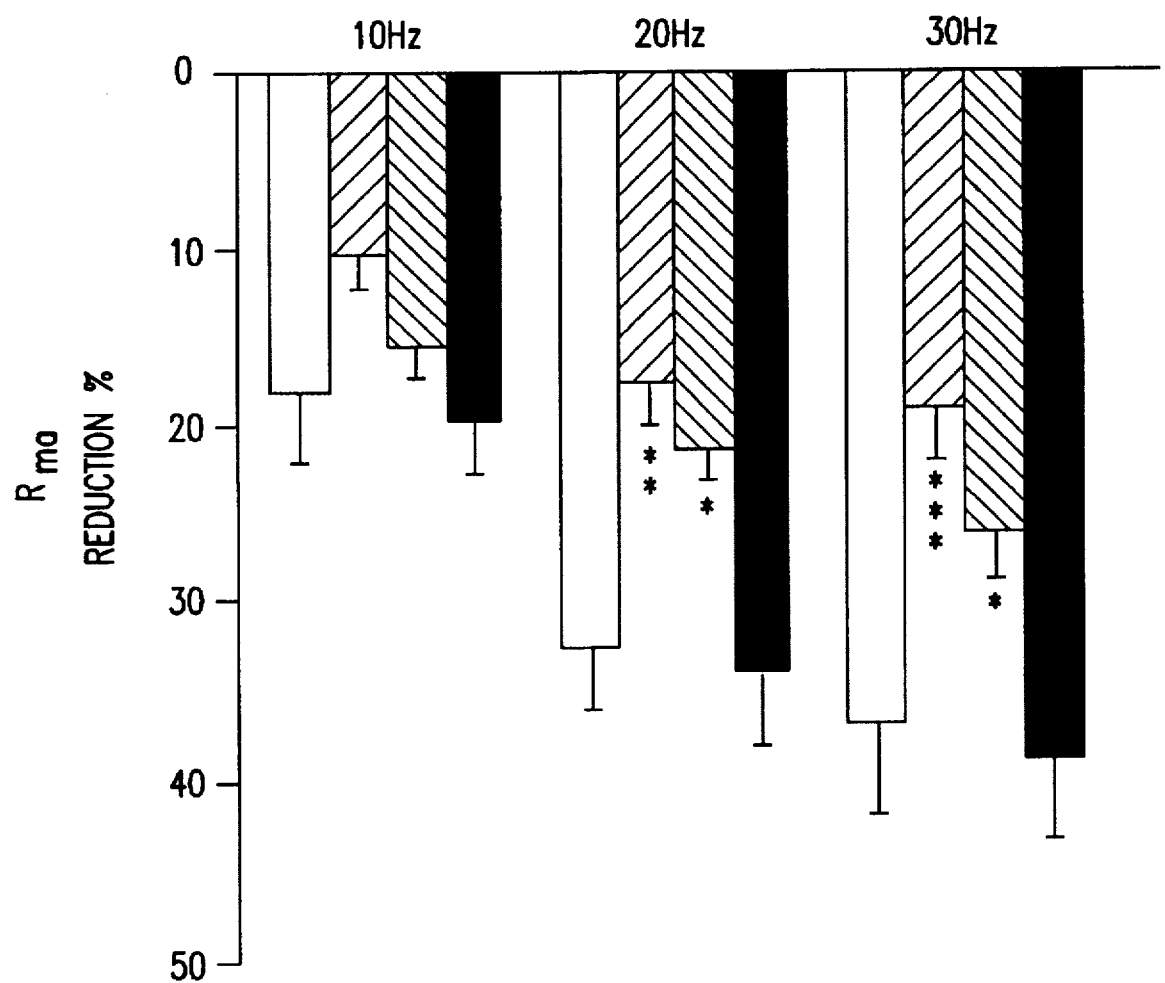

FIG. 7 Effects of parasympathetic nerve stimulation (5 V, 5 ms) at different frequencies on the vascular resistance in the internal maxillary artery ($R_{ma}$) of the cat pretreated with phentolamine (0.5 mg/kg/h), propranolol (1 mg/kg) and atropine (0.5 mg/kg) (open bar), just after the administration of exogenous NPY (8 nmol $kg^{-1}$, i.v.) (diagonal hatched bar), 30 min after the administration of NPY (cross hatched bar) and one hour later (solid bar). n=8, p<0.05 and p<0.01 when compared to the first column (one way ANOVA test).

FIG. 8 Recording from an anaesthetised dog showing changes in blood flow in the internal maxillary artery upon stimulation of the parasympathetic nerve (PS, 5 V, 5 m) at 30 Hz for 10 sec after pretreatment with phentolamine (0.5 mg/kg/h), propranolol (1 mg/kg) and atropine (0.5 mg/kg). In panel (a) the vasoconstrictor effect of the NPY analog [$Leu^{31}$, $Pro^{34}$] NPY ($Y_1$-receptor agonist, 8 nmol $kg^{-1}$) is similar to those of exogenous NPY shown in FIG. 1c) but has no influence on the subsequent parasympathetic vasodilatation. In panel (b) the administration of the NPY analog N-acetyl [$Leu^{28}$, $Leu^{31}$] NPY 24-36 ($Y_2$-receptor agonist, 20 nmol $kg^{-1}$) has no significant vasoconstrictor effect. However, the subsequent parasympathetic vasodilatation is reduced. One hour later, the effect of the parasympathetic stimulation is of the same magnitude as that before the administration of the $Y_2$-receptor agonist. Time scale is given by the PS stimulation for 10 sec.

Figure 9:
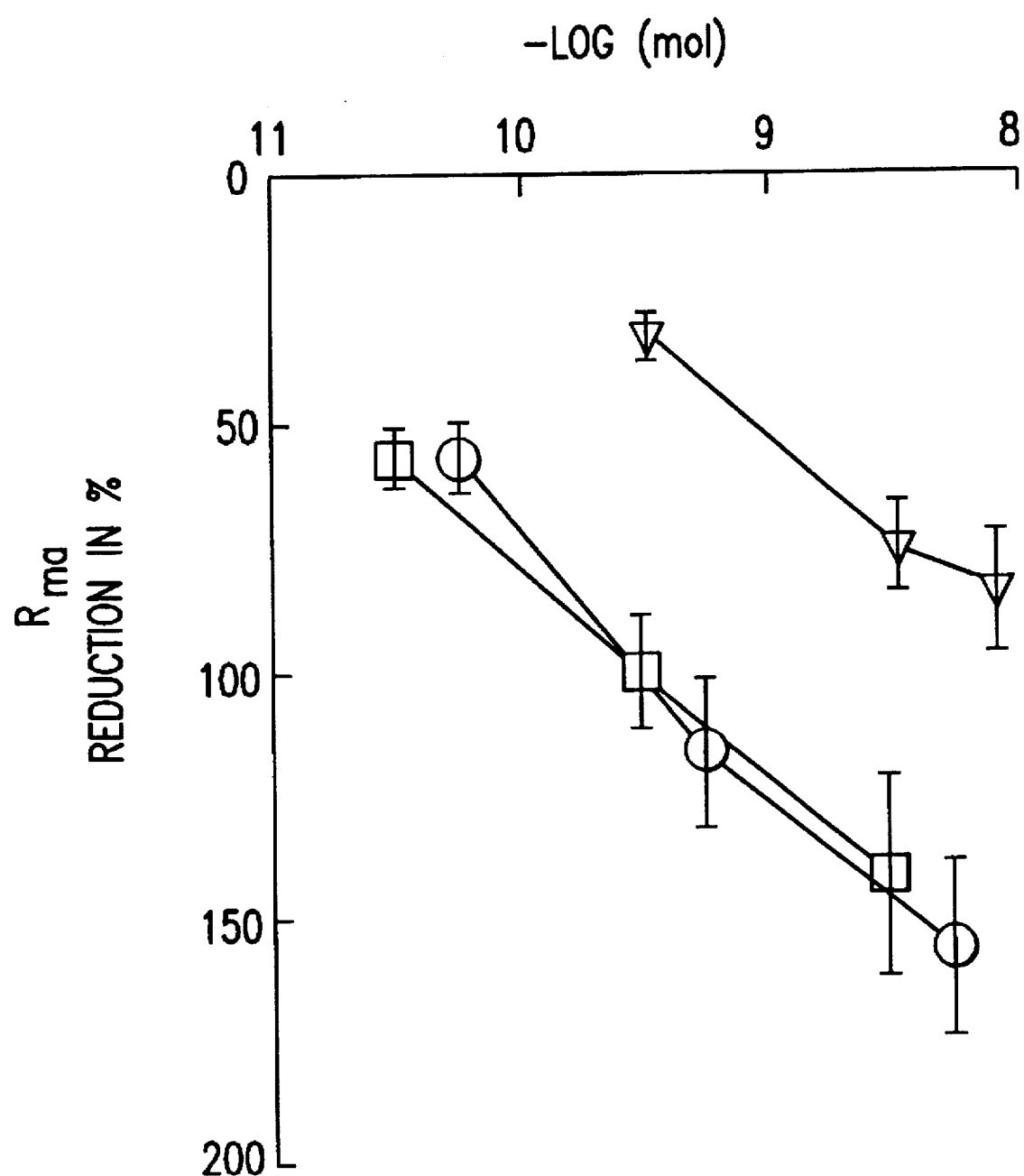

FIG. 9 Effects of local intra arterial injection of acetylcholine (Δ - - - Δ), vasoactive intestinal polypeptide (○ - - - ○) and peptide histidine isoleucine (□ - - - □) on the vascular resistance in the internal maxillary artery ($R_{ma}$) of the dog.

Materials and Methods

In vivo

Experiments were carried out on adult rats (Wistar) of both sexes (250–350 g), anaesthetised with sodium pentobarbitone (Nembutal, Boehringer-Ingleheim; 60 mg/kg, i.p.). The trachea was cannulated and the animal artifically ventilated. The femoral vein was cannulated for administration of peptides and further doses of anaesthetic. The left femoral artery was cannulated to record arterial pressure. Both vagus nerves were cut. This was done to eliminate vagally-mediated reflex effects on the heart which can occur when blood pressure is raised by neuropeptide Y. The cardiac end of the right vagus nerve was stimulated every 30 s with a 6 s train of supramaximal stimuli (2 Hz, 1 ms; 7 V) using an isolated, square-wave stimulator (Grass Instruments). The frequency was chosen to increase pulse interval by approximately 100 ms, a submaximal effect on this variable. The electrocardiogram was measured using needle electrodes and monitored on one channel of an osciloscope. Pulse interval (the period between successive beats of the heart) was recorded beat-by-beat by triggering from ECG. Pulse interval and arterial pressure were recorded on the pen recorder.

Dose-response curves were constructed from group data for all rats. Because of the long time-course of action of the peptides tested, not all peptides were given to each rat. Usually however, each rat received neuropeptide Y and two other peptides.

As an indication of prejunctional activity two parameters were measured; the maximum percent inhibition of the increase in pulse interval evoked by stimulation of the vagus nerve following injection of peptide (Δ pulse interval, % inhibition) and the time to half recovery of this effect (T50). For pressor action, an indicator of postjunctional activity, two parameters were also measured; the peak pressor response following injection of peptide (Δ blood pressure) and the duration of the increase in blood pressure (Duration). These indices give a reliable measure of the actions of a peptide at pre-and postjunctional sites, and have been used previously in this laboratory for this purpose (Gardner and Potter, 1988; Potter et al., 1989; Potter et al., 1991). Results were analysed using a one-way ANOVA (Zar, 1984).

In vitro

Peptide analogs were assayed for their ability to compete with radiolabelled peptide YY for binding sites on two human neuroblastoma cell lines expressing endogenous neuropeptide Y receptors. In addition, N-acetyl [$Leu^{28}$, $Leu^{31}$] neuropeptide Y-(24-36) was tested for its ability to stimulate increases in intracellular cytosolic calcium in Chinese Hamster Ovary (CHO) cells transfected with the human neuropeptide Y $Y_1$ receptor cDNA previously described (Herzog et al., 1992). The cell lines SK-N-MC (American Type Tissue Culture HTB10), which expresses neuropeptide Y receptors of the neuropeptide Y $Y_1$ receptor subtype, SMS-KN (kidney provided by Dr Thue Schwartz), which expresses neuropeptide Y receptors of the neuropeptide Y Y1 receptor subtype, SMS-KAN (kindly provided by Dr Thue Schwartz), which expresses neuropeptide Y receptors of the neuropeptide Y $Y_2$ receptor subtype, and the neuropeptide Y $Y_1$ receptor transfected CHO cells were maintained in 5% $CO_2$ in Dulbecco's modified Eagle's medium (DMEM)/HamsF-12 with 2 mM glutamine, 100 international units penicillin, streptomycin at 100 μg/ml, and 10% fetal calf serum. All media and materials for tissue culture were obtained from Cytosystems (Castle Hill, NSW, Australia). Cells were harvested by treatment with 0.2% EDTA in phosphate buffered saline and immediately used in the binding assay described.

Binding assays were performed as follows: Cells ($1 \times 10^6$) were incubated in 0.5 ml assay buffer (50 mM Tris-HCl, pH 7.4, 2 mM $CaCl_2$, 5 mM KCl, 120 mM NaCl, 1 mM $MgCl_2$ 0.1% bovine serum albumin in the presence of 0.05 nM {$^{125}$I}porcine-peptide YY (Dupont/NEN) and increasing concentrations of peptides. Cells were incubated with the radiolabelled peptide and competitor peptides for 1 hour at room temperature and pelleted in a microcentrifuge for 4 minutes. Radioactivity was measured for 1 min in a gamma counter. Binding data was analysed using the Inplot program (Graphpad).

CHO cells were transfected, using a modified calcium phosphate transfection method (Sambrook et al., 1989), with the cDNA NEO expression vector (Invitrogen, San Diego) containing the coding region of the human neuropeptide Y $Y_1$ receptor, as described (Herzog et al., 1992). Peptide YY, N-acetyl [$Leu^{28}$, $Leu^{31}$] neuropeptide Y-(24-36) or ATP (Sigma) at 1 μM were then tested for their ability to induce an increase in cytosolic calcium levels as measured with the calcium-sensitive fluorescent dye Fura-2 acetoxymethyl ester (Fura-2 AM, Molecular Probes). Cells were suspended in loading media (Modified RPMI, 10 mM Hepes, 1% newborn fetal calf serum) and incubated in a spinner flask at 37° C., for 2.5 hours at $1\times10^6$ cells/ml. Cells were then treated with 1 mM Fura-2 AM for 30 minutes at 37° C., washed twice with loading media and resuspended at $5\times10^6$ cells/ml. Immediately before use in fluorescence spectroscopy, cells were recovered by centrifugation at 1000 rpm and resuspended at $1\times10^6$ cells/ml in a modified Krebs buffer (135 mM NaCl, 4.7 mM KCl; 1.2 /nM $MgSO_4$, 1.2 mM $KH_2PO_4$, 5 mM $NaHCO_3$, 1 mM $CaCl_2$, 2.8 mM glucose, and 10 mM Hepes, pH 7.4) containing 1 mM sulphinpyrazone. Fluorescence recordings were made on an Hitachi fluorescence spectrometer (F4010) at 340 nm (excitation) and 505 nm (emission) over 10 minutes with slit widths of 5 nm and a response time of 2 seconds. Intracellular calcium levels were quantitated using equations described (Grynkiewicz et al., 1985).

Peptide Synthesis and Purification

Amidated peptides were synthesized on the Applied Biosystem (ABI) Peptide Synthesizer Model 430A using t-butyloxycarbonyl chemistry. Peptide synthesis was carried out in solid phase on p-methylbenzhydrylamino (MBHA) resin supplied by ABI. Hydrogen fluoride cleavage of the fully protected peptide from the solid support was performed by Auspep Pty Ltd, Melbourne. Briefly, the resin was treated for 60 min in 10 ml hydrogen fluoride with 1.3 g of phenol as a scavenger. Peptides were extracted into an aqueous phase (30% acetronitrile/water, v/v) and scavengers were washed out with ether. The aqueous extracts were then lyophilised to yield crude product. Side chain protection groups chosen for each amino acid were removed during the cleavage process. Peptides were purified by high performance liquid chromatography (Ion exchange and Reverse Phase) followed by sequence and amino acid analysis for sequence integrity.

Pure peptide (5 mg) was acetylated by being dissolved in 1 ml of water to which 5 ml of a mixture of acetic anhydride in methanol (1:3 v/v) was added. After 3 hours at room temperature, 10 mls of water was then added and the peptide lyophilised (Dill, 1986). Mass Spectroscopy—was carried out to measure the acetylation reaction. A mass ion (Mτ) of 1788 was obtained; molecular weight consistent with the predicted value of N-acetyl [$Leu^{28}$, $Leu^{31}$] neuropeptide Y-(24-36).

Peptides synthesized were neuropeptide Y, neuropeptide Y-(24-36), N-acetyl neuropeptide Y-(24-36), [$Leu^{28}$, $Leu^{31}$] neuropeptide Y-(24-36) and N-acetyl [$Leu^{28}$, $Leu^{31}$] neuropeptide Y-(24-36). All were tested for binding affinity to both cell lines in vitro and for pre- and postjunctional activity in vivo. Other peptides tested for binding activity were peptide YY, neuropeptide Y-(13-32), {$Leu^{17}$, $Gln^{19}$, $Ala^{21}$, $Ala^{22}$, $Glu^{23}$, $Leu^{28}$, $Leu^{31}$] neuropeptide Y-(13-36) (in some cases, peptide YY and neuropeptide Y were obtained from Auspep, Australia). Mepyramine (pyrilamine, Sigma: 10 mg/kg) were also used in some in vivo experiments.

Proton NMR Spectroscopy.

N-acetyl [$Leu^{28}$, $Leu^{31}$] neuropeptide Y-(24-36) was dissolved in 20% deuterated trifluoro-ethyl alcohol (90% $H_2O$/ 10% deuterated trifluoro-ethyl alcohol) to give a final concentration of 1.25 mM at pH 4.0 and 295 K. Sample pH was adjusted with dilue HCl and NaOH and measured with an Activon BJ51130 thin-stem NMR microelectrode and a Radiometer pHM-64 meter. Values of pH reported are meter readings uncorrected for the deuterium isotope effect. Samples were placed in 5 mm precision tubes.

NMR spectra were recorded at 400 MHz in the Fourier transform mode with quadrature detection using a Bruker AMX-400 spectrometer. The one-dimensional spectra were collected by using a 90° radio-frequency pulse of 5.8 μs. Spectral widths of 4.0 kHz were employed with a preacquisition delay of 2 s and a total of 256 summed FIDs were collected in 16 K dta points. The signal-to-noise ratio was about 350:1.

Spin systems were assigned using total correlation spectroscopy (TOCSY) spectra obtained with a MLEV-17 pulse sequence (Bax and Davis, 1985; Griesinger et al., 1988). The mixing time was 120 ms and the trim pulses were 2.5 ms. The spin-lock field strength was about 9 kHz. The water resonance was suppressed by continuous low-power (62 dB) irradiation throughout the relaxation period (1.8 s) and the mixing period by utilizing O1/O2 phase coherence (Zuiderweg et al., 1986). Two-dimensional nuclear Overhauser effect spectroscopy (NOESY) experiments (Jeener et al., Macura et al., 1981; Wüthrich, 1988) were recorded both for the purpose of obtaining proton-proton distance constraints and as an aid in making the resonance assignments sequence-specific. A mixing time of 300 ms was used to derive proton-proton distance constraints, a suitable compromise between avoidance of spin diffusion effects and cross-peak intensity. A total of 512 free induction decays, each consisting of 128-192 scans were acquired with an F2 time domain size of 4 K. Prior to Fourier transformation, the data were zero-filled and apodized using either a shield sine-bell function (4–5 in F2 and 2.0–2.5 in F1) or Gaussian multiplication in F2 (line broadening of −16 to −20 Hz, and GB of 0.16–0.2) and a shifted sine bell of 2–2.5 in F1. The spectra had a final processed time domain size of 4×1 K through zero filling using a Bruker X32 data station running under UNIX. Chemical shifts were referenced to internal trimethylsilylpropansulfonic acid.

Distance Geometry Calculations

NOE cross-peaks were subjected into four distance categories depending ion cross peak intensity. Strong NOEs were given an upper distance constraint of 0.3 nm, medium-NOEs wee given at value of 0.4 nm and weak NOEs were given a value of 0.45 nm. Corrections for pseudoatoms were applied wherever necessary. A total of 500 distance geometry structures were calculated from random starting structures using the program DIANA II (Güntert et al., 1991) on a Sun 2GX Sparkstation while molecular graphics were processed using the programs MidasPlus (Ferrin et al., 1988) or Insight 2 operating on a Silicon Graphics IRIS 4D workstation.

Results

To determine the specificity of action of the neuropeptide Y analogs on neuropeptide Y $Y_1$ and neuropeptide Y $Y_2$ receptor function in vivo, analogs were first tested for their ability to increase blood pressure through a neuropeptide Y $Y_1$-receptor mediated postjunctional effect and to inhibit neurotransmitter release through a $Y_2$ receptor-mediated prejunctional effect.

Actions in vivo

Figure 1A:
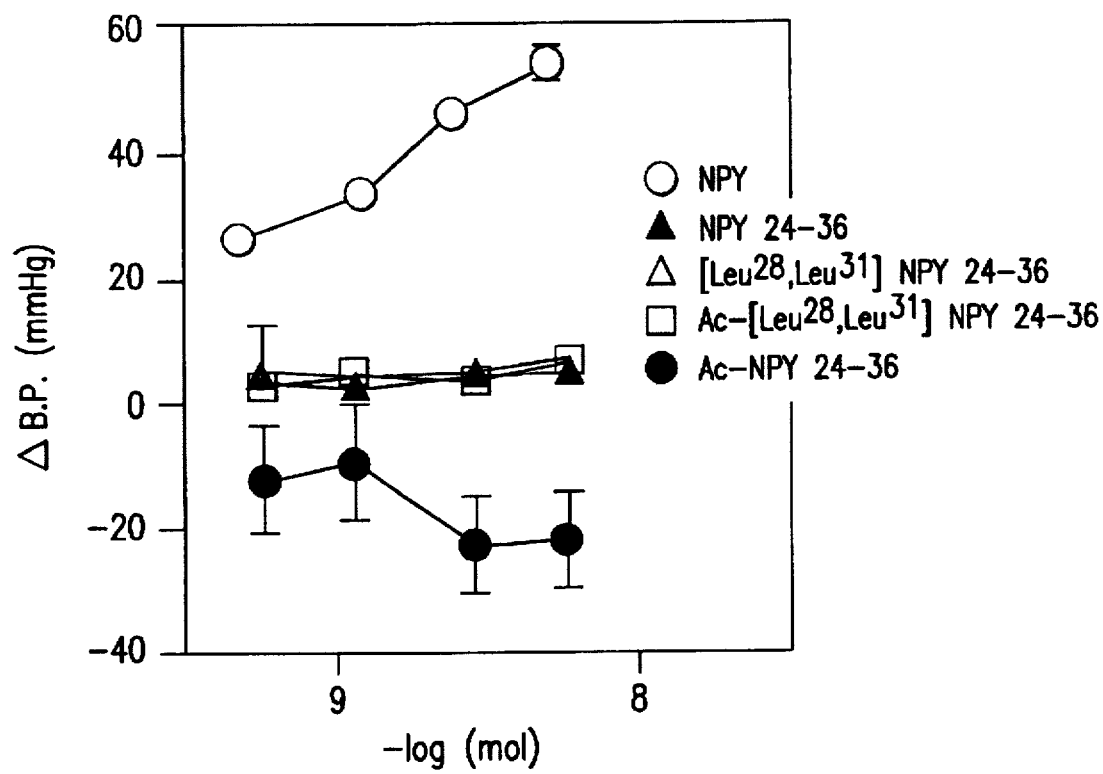
FIG. 1. Graphs show dose-response curves for neuropeptide Y (○), N-acetyl [Leu$^{28}$, Leu$^{31}$] neuropeptide Y-(24-36) (□), [Leu$^{28}$, Leu$^{31}$] neuropeptide Y-(24-36) (△), N-acetyl neuropeptide Y-(24-36) (●) and neuropeptide Y-(24-36) (▲). The two graphs in panel A on the left show the pressor effects of the two peptides; the peak pressor effect (top) and the duration of action (bottom). Neuropeptide Y (○) increases blood pressure in a dose dependent manner. N-acetyl [Leu$^{28}$ Leu$^{31}$] neuropeptide Y-(24-36) (△) and neuropeptide Y-(24-36) (▲) show no significant pressor effects. NOTE N-acetyl neuropeptide Y-(24-36) (●) has a depressor effect at all doses. The two graphs in panel B on the right show the vagal inhibitory or presynaptic effects of the peptides. Both neuropeptide Y (○) and N-acetyl [Leu$^{28}$, Leu$^{31}$] neuropeptide Y-(24-36) (□) inhibit cardiac vagal action for a prolonged period in a dose-dependent manner. The other analogs N-acetyl neuropeptide Y-(24-36) (●), neuropeptide Y-(24-36) (▲) and [Leu$^{28}$, Leu$^{31}$] neuropeptide Y-(24-36) (△) all have significant inhibitory or prejunctional actions but these effects are transient.

Five of the peptides were tested in vivo; another three relevant to this study (peptide YY, neuropeptide Y-(13-32), [$Leu^{17}$, $Gln^{19}$, $Ala^{21}$, $Ala^{22}$, $Glu^{23}$, $Leu^{28}$, $Leu^{31}$] neuropeptide Y-(13-36) had been tested extensively in vivo in a previous study (Potter et al., 1989). Neuropeptide Y was the only molecule of five tested in vivo which raised blood pressure significantly. Neuropeptide Y increased blood pressure in a dose-dependent manner as reported previously (e.g. Potter et al., 1989). N-acetyl [$Leu^{28}$, $Leu^{31}$] neuropeptide Y-(24-36), neuropeptide Y-(24-36) and [Leu$^{28}$, Leu$^{31}$] neuropeptide Y-(24-36) did not significantly increase blood pressure at any dose tested (ANOVA), while N-acetyl neuropeptide Y-(24-36) caused a slight decrease in blood pressure which was significant at higher doses (FIG. 1). In high doses neuropeptide Y has been reported to release histamine which subsequently decreases blood pressure (Grundemar et al., 1990a; 1991; Shen et al, 1991). This effect can be blocked by the H$_1$-receptor antagonist mepyramine. Although the doses of C-terminal fragment shown in the studies by Grundemar and colleagues were 2–5 times higher than those used here mepyramine was used to test whether the depressor effect evoked by N-acetyl neuropeptide Y-(24-36) was an indirect effect due to histamine release. However, this depressor effect was not blocked by mepyramine (10 mg/kg—data not shown). No depressor effects were observed after injection of any of the other fragments. The results for all analogs are shown in FIG. 1A.

As shown previously neuropeptide Y inhibits cardiac vagal action for a prolonged period by acting through a prejunctional (neuropeptide Y Y$_2$) receptor. Both the magnitude and duration of the inhibition are dose dependent. N-acetyl [Leu$^{28}$, Leu$^{31}$] neuropeptide Y-(24-36) also inhibited cardiac vagal action (FIG. 1). The magnitude and duration of this inhibition were not significantly different from neuropeptide Y except for the faster time to half recovery at the lowest dose (50 nmol). This can be seen in FIG. 1, Panel B (, N-acetyl [Leu$^{28}$, Leu$^{31}$] neuropeptide Y-(24-36). The other three analogs tested (Δ, [Leu$^{27}$, Leu$^{31}$] neuropeptide Y-(24-36)▲, neuropeptide Y-(24-36), ●, N-acetyl neuropeptide Y-(24-36)) also showed significant inhibitory effects on cardiac vagal action especially at the higher doses, but, these effects were of short duration. The EC$_{50}$ doses for the neuropeptide Y Y$_2$ effects (Δ pulse interval, T$_{50}$) are given in Table 1. These need to be compared to the absolute responses seen in FIG. 1. For example N-acetyl neuropeptide Y-(24-36) has a similar EC$_{50}$ for Δ pulse interval and T$_{50}$ to neuropeptide Y. However, the effect is transient at all doses, 2–4 min for N-acetyl neuropeptide Y-(24-36) compared to 6–13 min for neuropeptide Y.

TABLE 1

Neuropeptide Y Y$_2$ in vivo Effects
EC$_{50}$ for Δ pulse interval and T$_{50}$ for neuropeptide Y and analogs

|  | Δ Pulse Interval | T$_{50}$ |
|---|---|---|
| Neuropeptide Y | 9.14 ± 0.2 | 8.5 |
| N-acetyl [Leu$^{28}$, Leu$^{31}$] neuropeptide Y-(24-36) | 8.5 ± 0.2 | 8.6 ± 0.15 |
| N-acetyl neuropeptide Y-(24-36) | 8.9 ± 0.4 | 8.5 ± 0.15 |
| [Leu$^{28}$, Leu$^{31}$] neuropeptide Y-(24-36) | 08.7 ± 0.4 | —* |
| Neuropeptide Y-(24-36) | 8.4 ± 0.2 | —* |

EC$_{50}$ is defined as the -log of the dose which evokes 50% of the maximum response.
Mean ± SEM of results from five rats.
*response only transient (< 2 mins) so no EC$_{50}$ calculated.

Actions in vitro

Figure 2A:
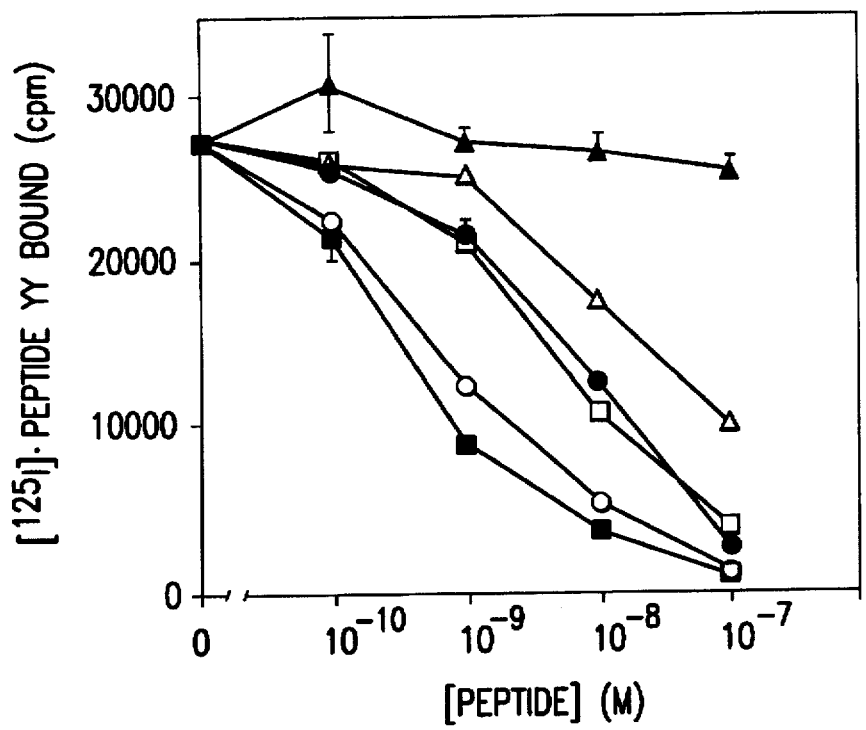
FIG. 2. Inhibition of [$^{125}$I]-PYY binding to neuropeptide Y Y$_2$ and Y$_1$ receptors with various neuropeptide Y-related peptides indicates specific Y$_2$ receptor analogs.
Figure 2B:
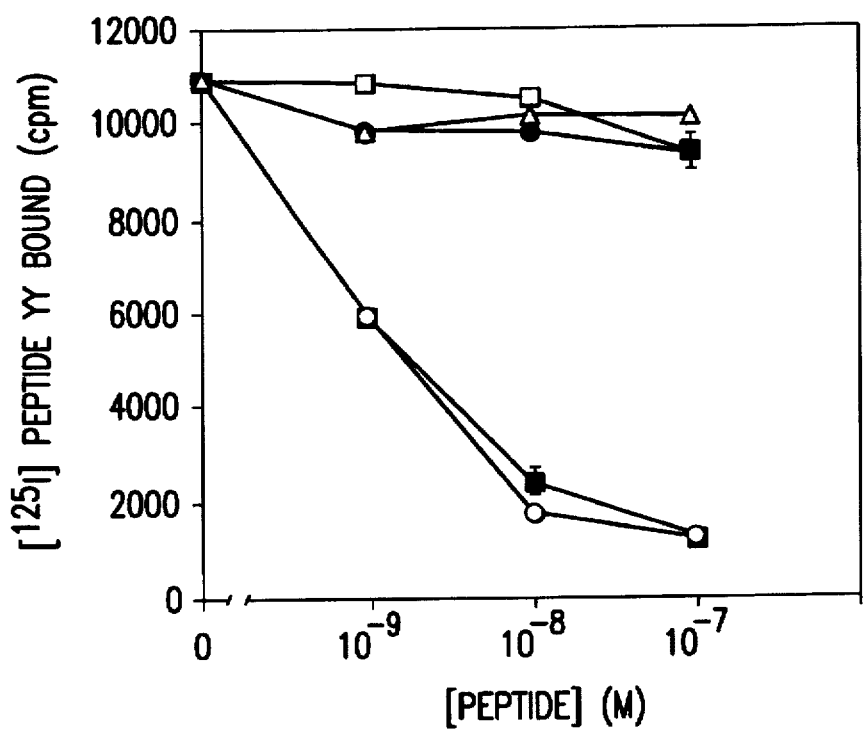

With the availability of cell lines expressing both the neuropeptide Y Y$_1$ and neuropeptide Y Y$_2$ receptor subtypes, the present inventors next tested the ability of the neuropeptide Y analogs to compete for radiolabelled peptide YY in an in vitro binding assay. Two cell lines were used for comparison of neuropeptide Y related analogs. The human neuroblastoma SMS-KAN cell line has been shown to express only the neuropeptide Y Y$_2$ receptor subtype. In this cell line, peptide YY and neuropeptide Y compete for radiolabelled peptide YY and an IC$_{50}$ of 0.5±0.1 nM and 0.8±0.1 nM, respectively (FIG. 2, and table 2). The IC$_{50}$ for N-acetyl [Leu$^{28}$, Leu$^{31}$] neuropeptide Y-(24-36) is 3.9±0.4 nM (n=3), while that of [Leu$^{28}$, Leu$^{31}$] neuropeptide Y 24-36 is reduced a further three-fold 12.7+1.2 nM (n=3). Other commonly used analogs have also been used for comparison. Neuropepetide Y-(13-32) which is inactive in vivo (Potter et al., 1989) also showed little binding in this cell line. No IC$_{50}$ was calculated for this analog. Neuropeptide Y and peptide YY also competed for radiolabelled peptide YY binding to the cell line, SK-N-MC, which expresses only the Y$_1$ receptor. However neither N-acetyl [Leu$^{28}$, Leu$^{31}$] neuropeptide Y-(24-36) or [Leu$^{28}$, Leu$^{31}$] neuropeptide Y-(24-36) shoed significant binding (see FIG. 2).

TABLE 2

Neuropeptide Y Y$_2$- receptor Binding
[IC$_{50}$ Values for neuropeptide Y analog competition of radiolabelled peptide YY Bound to SMS-KAN Cells

| Peptide | IC$_{50}$ (nM) |
|---|---|
| Peptide YY | 0.5 ± 0.1 |
| Neuropeptide Y | 0.8 ± 0.1 |
| N-acetyl [Leu$^{28}$, Leu$^{31}$] neuropeptide Y-(24-36) | 3.9 ± 0.4 |
| [Leu$^{28}$, Leu$^{31}$] neuropeptide Y-(24-36) | 12.7 ± 1.2 |
| N-acetyl neuropeptide Y-(24-36) | 14.5 ± 1.5* |
| [Leu$^{17}$, Gln$^{19}$, Ala$^{21}$, Ala$^{22}$, Glu$^{23}$, Leu$^{28}$, Leu$^{31}$] neuropeptide Y-(24-36) | 7.3 ± 0.7 |

IC$_{50}$ is defined as the concentration of peptide required to achieve 50% inhibition of binding. IC$_{50}$ values were obtained from analysis of binding data using the Inplot program (Graphpad). Values were the average of three determinations, except neuropeptide Y and N-acetyl neuropeptide Y-(24-36) with n=2, and means and standard deviation are given.*

Figure 3A:
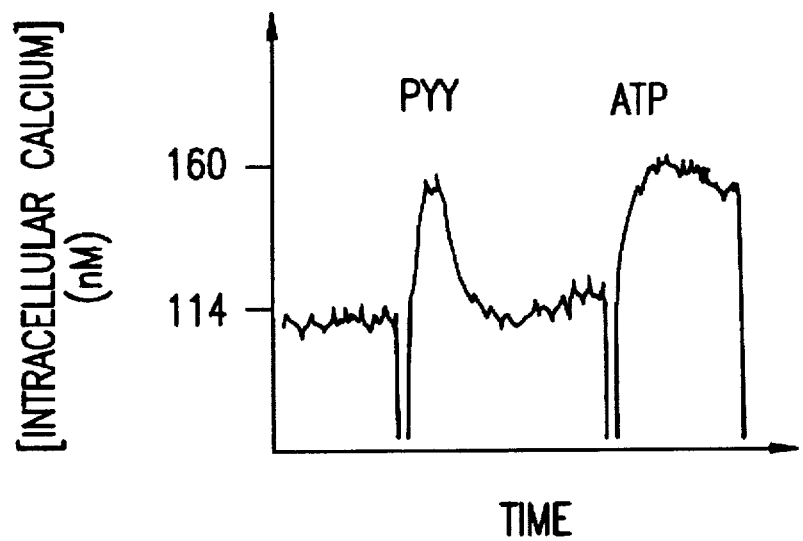
Figure 3B:
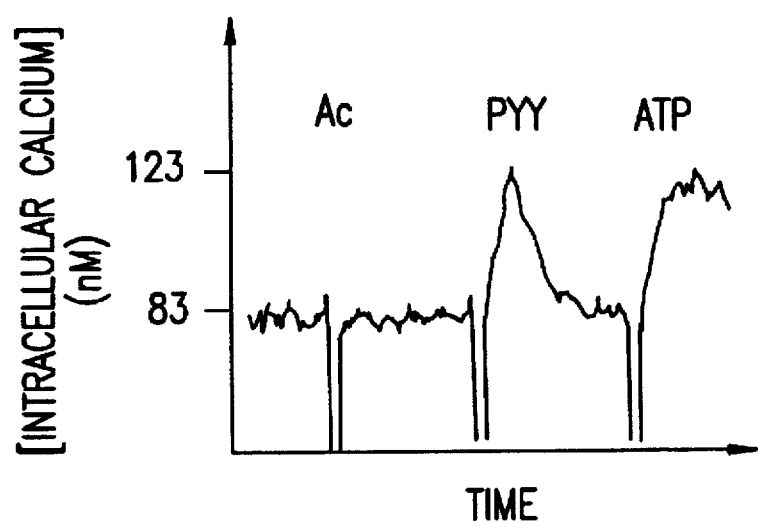

Results of the binding studies would predict that both N-acetyl [Leu$^{28}$, Leu$^{31}$] neuropeptide Y-(24-36) and [Leu$^{17}$, Gln$^{19}$, Ala$^{21}$, Ala$^{22}$, Glu$^{23}$, Leu$^{28}$, Leu$^{31}$] neuropeptide Y-(13-36) should show no activity on the neuropeptide Y Y$_1$ receptor. However, as demonstrated in vivo previously, while [Leu$^{17}$, Gln$^{19}$, Ala$^{21}$, Ala$^{22}$, Glu$^{23}$, Leu$^{28}$, Leu$^{31}$] neuropeptide Y-(13-36) was a good agonist at the neuropeptide Y Y$_2$ receptor, it also induced substantial pressor effects, presumably acting through the neuropeptide Y Y$_1$ receptor subtype. Therefore, the present inventors tested effects of N-acetyl neuropeptide Y-(24-36), neuropeptide Y, and peptide YY on a functional response mediated by the neuropeptide Y Y$_1$ receptor in vitro. Both peptide YY and [Leu$^{17}$, Gln$^{19}$, Ala$^{21}$, Ala$^{22}$, Glu$^{23}$, Leu$^{28}$, Leu$^{31}$] neuropeptide Y-(13-36) have been tested previously in vivo and are included here for comparison of the neuropeptide Y-(24-36) group of analogs. Peptide YY and neuropeptide Y previously been shown to stimulate increases in intracellular cytosolic calcium acting through the cloned human neuropeptide Y Y$_1$ receptor subtype expressed in a fibroblast Chinese Hamster Ovary (CHO) cell line (Herzog et al., 1992). Human neuropeptide Y Y$_1$ receptor-transfected CHO cells loaded with the calcium-sensitive dye Fura-2 AM responded to μM of either neuropeptide Y or peptide YY, with increase in intracellular cytosolic calcium of 39.4 nM and 71.2 nM, respectively, over baseline values (FIGS. 3A and 3B). However, N-acetyl [Leu$^{28}$, Leu$^{31}$] neuropeptide Y-(234-36)

(1 μM) did not induce a rise in intracellular calcium, even though ATP (1 μM), acting through an endogenous ATP receptor, induced an increase in cytosolic calcium to, 33.8 nM. The neuropeptide Y $Y_1$ receptor-specific analog [Leu[31], Pro[34]] neuropeptide Y has been shown previously to stimulate increases in cytosolic calcium levels through the cloned neuropeptide Y $Y_1$ receptor (Herzog et al, 1992).

Solution Structure

An investigation of the solution structure by NMR of N-acetyl [Leu[28], Leu[31]] neuropeptide Y-24-36) was also made in 20% trifluoro-acetyl alcohol. His[26], Asn[29], Thr[32] and Gln[34] could be assigned sequence specifically from the spectrum due to their uniqueness. Connectivities from the 4 unique spin systems were available for entry points in the sequence specific assignment analysis based on the comparison of the TOCSY assignments of amino acid residue type and the short-range NOESY assignments of short observable distances between adjacent residues including the NM, Ha and Hb protons of residue (i) to the NH proton of residue (i+1) (Wüthrich, 1986; Wüthrich, 1988). NOESY couplings in the fingerprint region between the $α_i$CH proton and the $N_{i+1}$H protons from sequential residues and between sequential NHJ protons were used to specifically verify the assignment of the non-unique spin systems.

A summary of the observed sequential and medium-range inter-residue backbone NOEs is shown in FIG. 4 with the amino acid sequence presented in single letter code. An asterix indicates the likely presence of an NOE which cannot be detected due to overlap. The thickness of the NOE line reflects the distance category with NOE distances in the <0.3 nm range represented by the thickest lines and the <0.45 nm distances represented by the thinnest lines. Weak or absent sequential $α_i/N_{i+1}$ couplings combined with strong sequential $N_i/N_{i+1}$ couplings are indicators of the presence of α-helix (Wüthrich, 1986). This is supported by the pattern and intensity of medium-range NOEs from Ac-Leu[24] to Leu[30]/Leu[31] and together with the intensity of the $N_iH/N_{i+1}$H NOEs, the data are indicative of the presence of three loops of a α-helix.

A total of 77 upper distance constraints were used in the distance geometry algorithm DIANA II (Güntert et al., 1991) to generate 1000 structures from random starting conformations. These calculations yielded 14 structures which satisfied all the NMR distance constraints within 5 pm and which had the lowest penalty values. All members of the final group of non-violated structures displayed good covalent geometry. A stereo view of the structures in the final group superimposed over the backbone atoms is shown in FIG. 5 revealing three loops of helix. The root mean square deviations (RMSDs) between the 14 structures range from 9–53 pm.

Discussion

The present inventors have synthesized analogs of neuropeptide Y which show selective prejunctional (neuropeptide Y $Y_2$) activity in anaesthetised rats. The two analogs contain thirteen amino acids. Earlier work with a longer fragment of this analog, [Leu[17], Gln[19], Ala[21], Ala[22], Glu[23], Leu[31]] neuropeptide Y-(13-36) showed that this molecule retained full prejunctional activity in our in vivo studies (Potter et al., 1989). It did, however, also retain significant pressor activity and so we proceeded with removal of further N-terminal amino acids with the aim of abolishing all postjunctional activity. Although attenuation of cardiac vagal action was retained in this analysis the effect was only transient. Other short C-terminal fragments (neuropeptide Y-(24-36), neuropeptide Y-(25-36), neuropeptide Y-(26-36) when used up to 3 μM have shown little prejunctional activity in in vitro assays (Grundemar et al, 1990b; 1991; 1993). As shown here the effects of the 24–36 fragments are only transient and this may account for differences seen 'in vitro'. It is possible also that the vas deferens prejunctional neuropeptide Y receptor may be different from the heart vagal prejunctional neuropeptide Y receptor (see Potter et al, 1992). When both neuropeptide Y-(24-36) and [Leu[28], Leu[31]] neuropeptide Y-(24-36) were acetylated the duration of the prejunctional activity was significantly increased. Nanomolar concentrations of the stabilised N-acetyl [Leu[28], Leu[31]] neuropeptide Y-(24-36) evoked prejunctional (vagal inhibitory) effects, which in both magnitude and duration of action were not significantly different from the prejunctional effects of neuropeptide Y. There was no demonstrable pressor (or neuropeptide Y $Y_1$) effect of the analog across this dose range. N-acetyl neuropeptide Y-(24-36) evoked a decrease in blood pressure at all doses. This was not due to histamine release and is concluded to be a direct effect of this analog. The mechanism of this depressor effect is currently being pursued.

It has been suggested that peptides like neuropeptide Y interact with cell membranes which stabilize their secondary structure before actually binding to their various receptors (Sargent and Schwyzer, 1986). Lipid vesicles mimic the action of the cell membrane and the secondary structure of neuropeptide Y in the presence of various lipid vesicles or trifluoro-ethyl alcohol appears to be similar (Cohune et al., 1991; Neugerbauer et al., 1992). Consequently, the stabilized structure reported here is expected to mimic the structure adopted by the peptide in the vicinity of the prejunctional neuropeptide Y $Y_2$ receptor. The determination of the structure of neuropeptide Y in solution is a necessary precursor for understanding the structure-activity relations of the peptide.

Projection of the α-helical sequence N-acetyl [Leu[28], Leu[31]] neuropeptide Y-(24-36) onto a helical wheel reveals that the structure is amphiphilic from 24–34 with Leu[24], Tyr[27], Leu[28], Leu[30] and Leu[31] on one face and Arg[25], His[26], Asn[29] and Arg[33] on the opposite face. This region probably constitutes the bulk of the neuropeptide Y $Y_2$ receptor binding site or at least promotes receptor recognition of the peptide. Arg[35] appears on the hydrophobic face at the C-terminal end of the helix. It may prove interesting to determine the importance of this charged residue for prejunctional activity. The structure of N-acetyl[Leu[28], Leu[31]] neuropeptide Y-(24-36) appears largely consistent with the structure of neuropeptide Y-(1-36) determined in water and containing the native Ile[28] and Ile[31] residues (Darbon et al., 1992). The link detected in the C-terminal helix in the earlier study at Tyr[27]/Ile[28] is not present in the stabilized peptide containing the Leu-Ile substitutions.

This is the first demonstration of an analog which mimics physiological effects of neuropeptide Y (both in magnitude and duration) on the prejunctional or neuropeptide Y $Y_2$ receptor. The binding studies show that the analog N-acetyl [Leu[28], Leu[31]] neuropeptide Y-(24-36) competes for the binding of radiolabelled peptide YY to neuropeptide Y $Y_2$ receptors on SMS-KAN cells with an $IC_{50}$ of 3.9+0.4 nM (n=3) which is similar to [Leu[17], Gln[19], Ala[21], Ala[22], Glu[23], Leu[28], Leu[31]] neuropeptide Y-(13-36) (ANA neuropeptide Y-(13-36): $IC_{50}$=7.3+0.7 nM; n=3). Both analogs show little binding to neuropeptide Y $Y_1$ receptors in SK-N-MC cells.

In the light of these results the ability of the neuropeptide Y Y2 agonists to effect vasodilation in vivo was examined.

Methods

Experiments were performed on twelve adult mixed breed dogs of both sexes weighing between 4 and 9 kg. These experiments were approved by the institutional animal care and ethics committee. The dogs were anaesthetised with pentobarbitone sodium (35 mg $kg^{-1}$ i.v.). The trachea was cannulated low in the neck and the animals were artifically ventilated. A catheter connected to a Statham P23AC blood pressure transducer was placed in a femoral artery for systemic blood pressure monitoring. Another catheter was inserted in a femoral vein for administration of compounds and further doses of anaesthetic as required (0.5–1 ml of a 1-in-5 dilution of pentobarbitone). The left cervical vagus nerve was dissected high in the neck, the vagal sheath was removed and then the sympathetic nerve was separated from the vagal trunk. In some animals the sympathetic nerve as traced to the superior cervical sympathetic ganglion (Berridge and Roach, 1986). The left zygomatic arch was removed and the vidian nerve and the sphenopalatine ganglion were exposed by a procedure similar to the one described by Eccles & Wilson (1973). Bipolar platinum electrodes connected to a Grass S 88 stimulator (Grass Instruments, Quincy, USA) were used for stimulation of the proximal portion of the cervical sympathetic nerve and the cut peripheral end of the parasympathetic nerve. The identification of cervical sympathetic nerve was confirmed by observing dilation of the pupil with its electrical stimulation. The left external carotid artery was disserted up to the internal maxillary artery. The main arterial branches located beyond to the superficial temporal artery were ligated as described previously by Lacroix et al. (1988), a procedure which leaves the internal maxillary artery flow supplying only the nasal mucosa. The superficial temporal artery was cannulated for selective injection of agents into the main nasal arterial blood supply. The nasal arterial blood flow was recorded with a transonic flow probe (3SB454) placed around the internal maxillary artery and connected to a T206 ultrasonic blood flowmeter (Transonic System Inc., N.Y., U.S.A.). All parameters were continuously recorded on a Grass polygraph model 7C in all experiments. The animals were allowed a one hour intervention-free period following completion of surgery.

Experimental Protocol

Group 1 (n+8): Solutions of ACh ($5.5 \times 10^{-11}$ to $5.5 \times 10^{-8}$ mol), VIP ($3 \times 10^{-11}$ to $3 \times 10^{-9}$ mol), PH1 ($3.3 \times 10^{-11}$ to $1.6 \times 10^{-8}$ mol) and NA ($6 \times 10^{-11}$ mol to $6 \times 10^{-8}$ mol) in 1 ml of saline, were infused into the superficial temporal artery over a period of 15 sec. The administration of saline alone had no measurable effect. An interval of 5 min was allowed between successive injections. Fifteen minutes after the completion of the ACh, VIP, PH1 and NA injections, parasympathetic nerve stimulations (5 V, 5 ms) were performed at continuous frequencies of 10, 20 and 30 Hz, each for 10 sec. Each stimulation was performed 3 min after the blood flow in the internal maxillary artery returned to base line from the preceding stimulation. Sympathetic nerve stimulation (15 V, 5 ms) was then performed continuously at 10 Hz for 3 min. Parasympathetic nerve stimulations were repeated five minutes, thirty minutes and then one hour after sympathetic nerve stimulation. This entire protocol was repeated after pretreatment with the α-adrenoceptor antagonist phentolamine (0.5 mg $kg^{-1}$ $h^{-1}$), the β-adrenoceptor antagonist propranolol (1 mg $kg^{-1}$) and the parasympathetic muscarinic receptor blocker atropine (0.5 mg $kg^{-1}$), all delivered by local intra arterial (i.a.) injection. Stimulations of the parasympathetic nerve were also performed five minutes, thirty minutes and one hour after the administration of exogenous NPY (8 nmol $kg^{-1}$) dissolved in 5 ml of saline and infused into the femoral vein for 1 min.

Group 2 (n=4): The parasympathetic nerve as stimulated at 10, 20 and 30 Hz in animals under control conditions and after pretreatment with phentolamine, propranolol and atropine (same doses as above). Parasympathetic nerve stimulations were repeated 5 min, 30 min and 1 hour after the i.v. administration of the NPY analog [Leu$^{31}$, Pro$^{34}$] NPY ($Y_1$-receptor agonist, 8 nmol $kg^{-1}$). Ninety minutes later, parasympathetic nerve stimulation was also performed after the i.v. infusion of the NPY analog N-acetyl [Leu28, Leu31] NPY 24–36 (Y2-receptor agonist, 20 nmol $^{kg-}1$).

Analysis of results: changes of the nasal arterial blood flow were expressed in terms of vascular resistance in the maxillary artery ($R_{ma}$), obtained by dividing the driving mean arterial blood pressure in the femoral artery by the peak value of the blood flow volume rate in the maxillary artery. Before each experiment a zero flow in the maxillary artery was obtained by clamping the artery upstream to the transonic probe for 30 sec. The duration of the responses were given in second sand calculated from the end of the electrical stimulation until return to former basal values. All data are presented as mean ± standard error of the man. Statistical differences were evaluated using one way ANOVA test.

Drugs Used

The following drugs were used: pentobarbitone sodium (Nembutal, Boehringer Ingelheim, Australia), acetylcholine (ACh, acetylcholine chloride, Sigma, U.S.A.). VIP (Peninsula, U.S.A.) and PHI (porcine PHI-27, Bachem, U.S.A.); phentolamine (Regitine, Ciba-Geigy, Switzerland), propranolol (Inderal, ICI, UK) atropine (Atropine sulfate, Astra, Sweden), NA (Levophed, Winthrop, Australia) and NPY (h-NPY, AUSPEP, Australia), $Y_2$ receptor agonist N-acetyl [Leu28, Leu31] NPY 24–36 (AUSPEP, Australia), and $Y_1$ receptor agonist [Leu$^{31}$, Pro$^{34}$] NPY (AUSPEP, Australia), and chlorisondamine (Ecolid, Ciba-Geigy, Switzerland). All solutions were freshly prepared before each experiment by dissolving the compounds in sterile 0.9% w/v NACl.

Results

The basal blood flow in the internal maxillary artery of the dog was 8.5±2 ml min $^{-1}kg^{-1}$. After section of both sympathetic and parasympathetic nerves on the left side the homolateral nasal arterial flow was 9.7±2.5 ml min$^{-1}k^{-1}$ (representing a 14% increase). The femoral arterial blood pressure was not modified by the section of the sympathetic or the parasympathetic nerves.

Figure 5A:
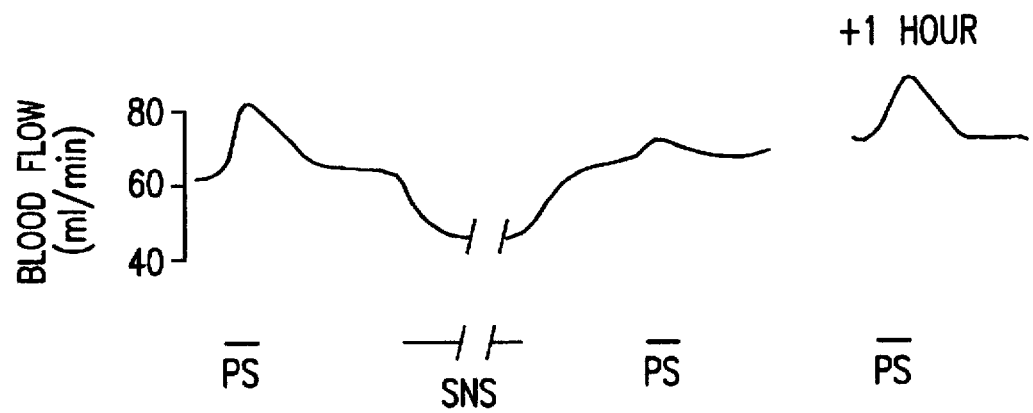
Figure 6A:
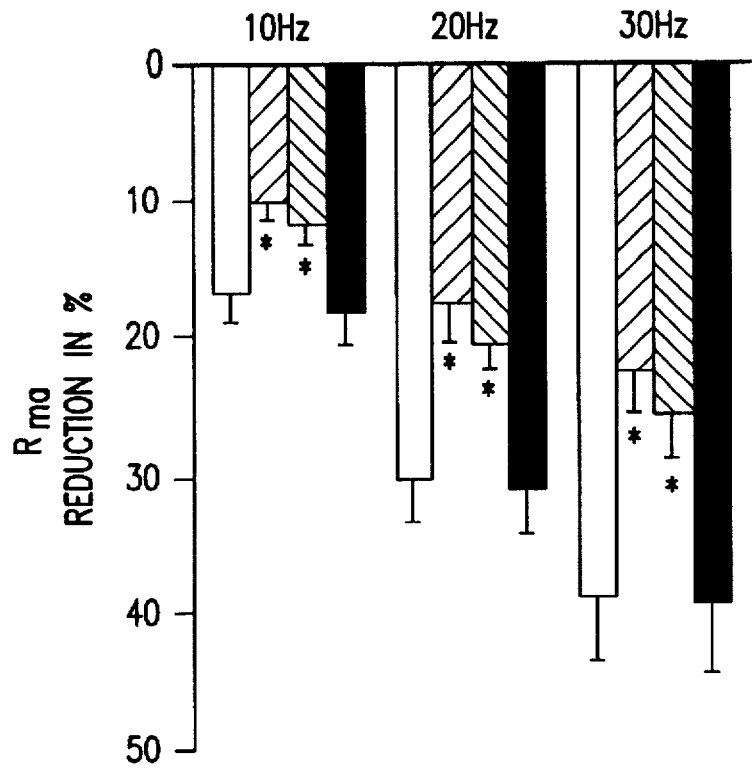

Electrical stimulation of the parasympathetic nerve induced frequency-depending reductions of the $R_{ma}$ (FIG. 5a and 6a) whereas the BP was not significantly modified (not shown). Parasympathetic stimulation at 10 Hz increased the blood flow from 9.7±2.5 ml min$^{-1}$kg$^{-1}$ to 11.35±1.8 ml min$^{-1}$kg$^{-1}$ representing a reduction in $R_{ma}$ OF 16.8±2% (FIG. 6a). during stimulation at 30 Hz the blood flow increased to 13.4±1.8 ml/min/kg corresponding to a Rma reduction of 38.5±4.7% (FIG. 6a). The blood flow increase lasted for 43±5 sec after stimulation at 10 Hz and 78±8.2 sec after 30 Hz stimulation.

Sympathetic nerve stimulation at 10 Hz for 3 min reduced the blood flow in the maxillary artery by 57.5±7% lasting more than 7 min. The vasodilator responses evoked by electrical stimulations of the parasympathetic nerve were attenuated by an average 40% (P<0.05) after sympathetic nerve stimulation at 10 Hz for 3 min (FIG. 6a). Thirty minutes after the SNS the vasodilatation evoked by the stimulation of the parasympathetic nerve was still significantly reduced by 23±5% (FIG. 6a). One hour after the completion of the SNS, the vasodilator effect of parasympathetic nerve stimulations were not significantly different in magnitude to those before sympathetic stimulation (FIG. 5a and 6a ).

Figure 5B:
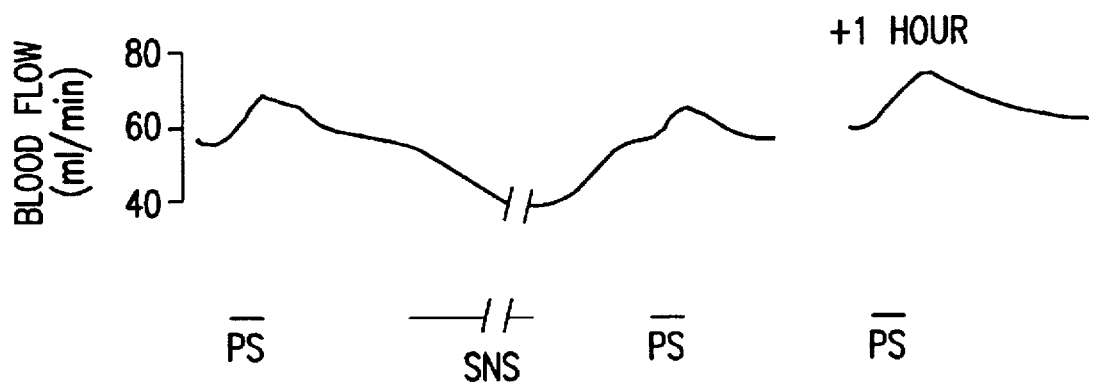
Figure 6B:
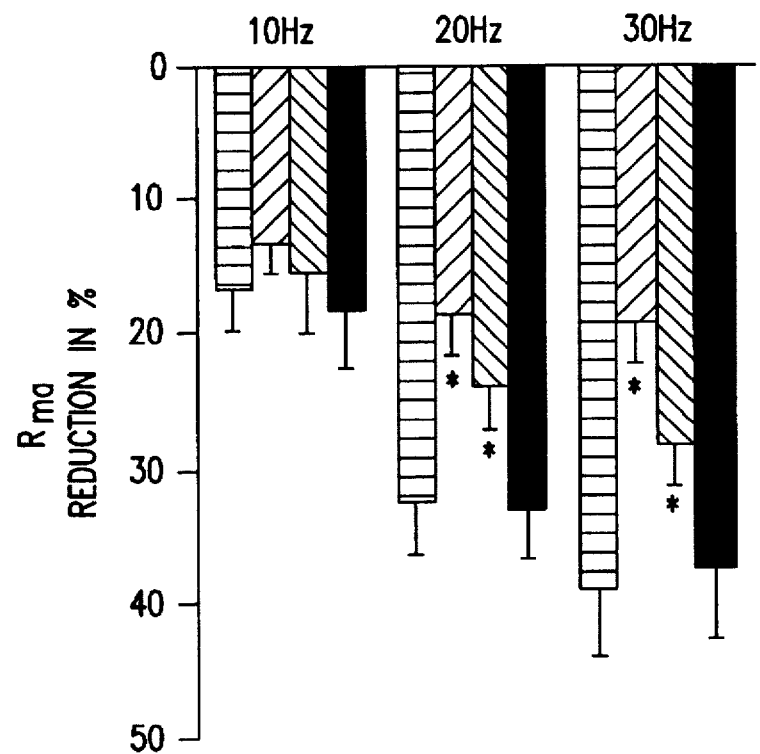

After combined pretreatment with phentolamine, propranolol and atropine the driving mean arterial blood pressure was reduced by 18±6%. In parallel, the blood flow in the internal maxillary artery was reduced by the same magnitude so the Rma was not significantly modified. The vascular effects of exogenous NA and ACh were virtually abolished in pretreated animals (not shown). The vasodilator responses to parasympathetic nerve stimulations were slower in onset and prolonged by 55% when compared to control (FIG. 5b). However, the peak value of the response were not significantly different to those observed before the administration of the adrenoceptor blockers and atropine (FIG. 6b).

Figure 1B:
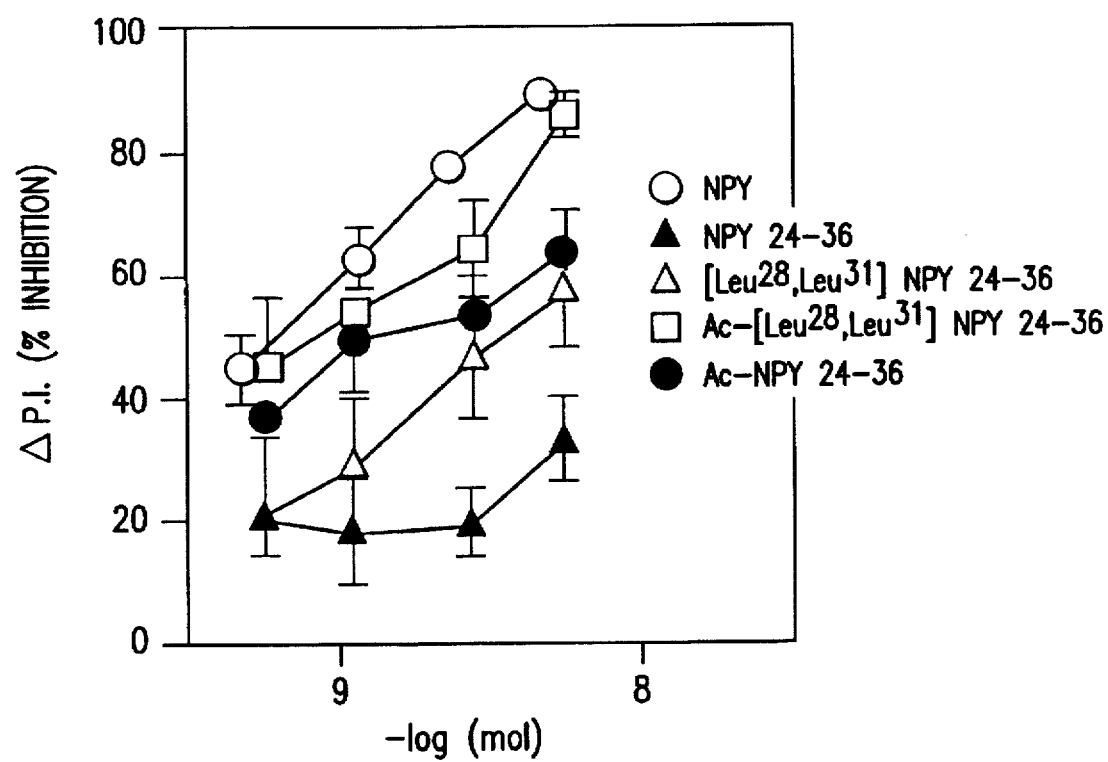
Figure 1C:
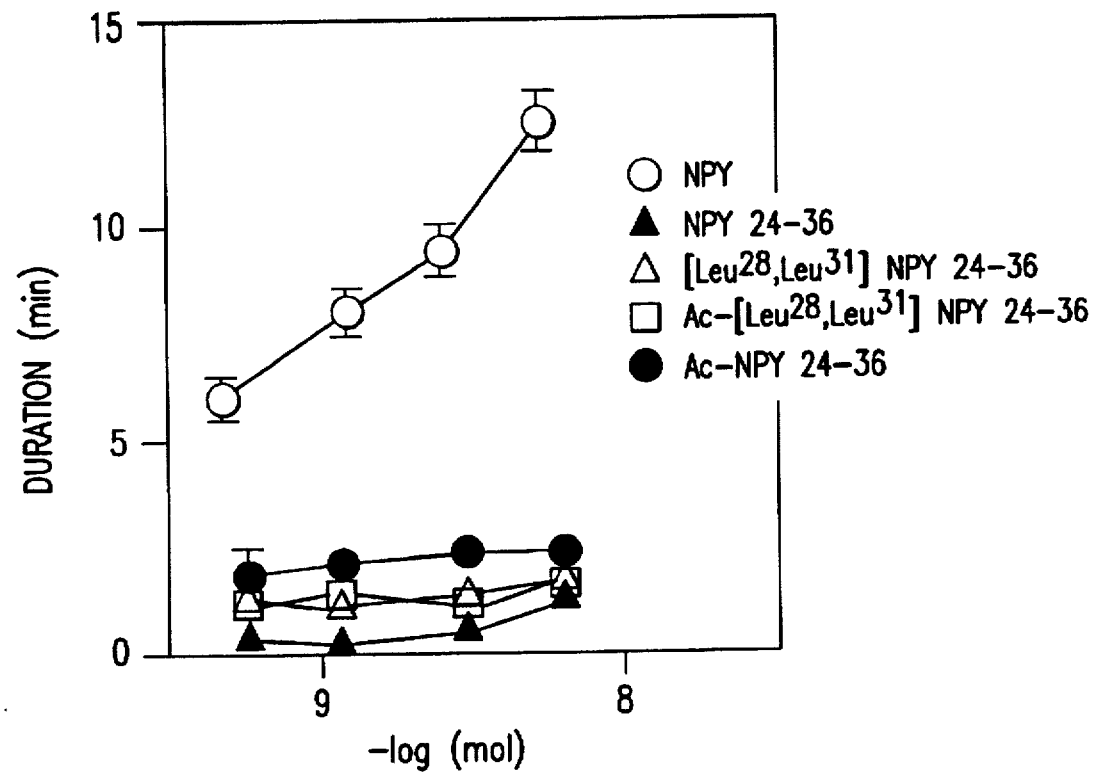
Figure 1D:
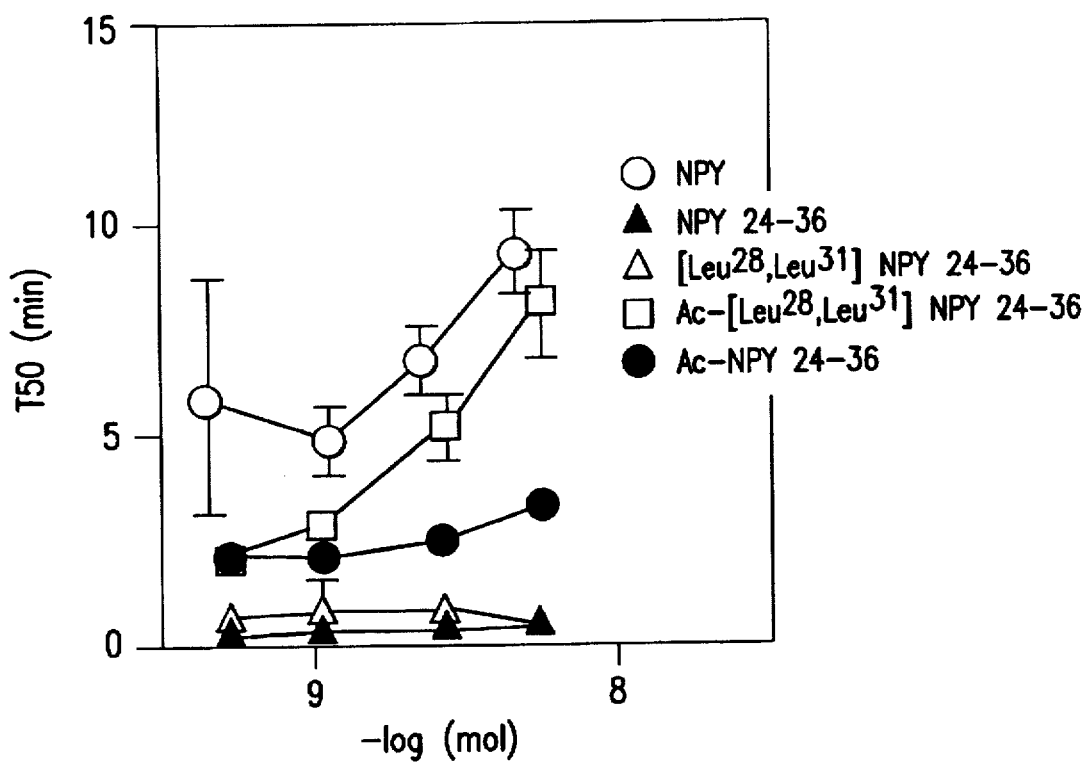

After adrenoceptor blockage, the vasoconstriction evoked by sympathetic stimulation at 10 Hz for 3 min was reduced by an average 35% when compared to control (FIG. 5b). The subsequent atropine-resistant vasodilatation evoked by parasympathetic nerve stimulations at 30 Hz and 30 Hz were reduced by approximately 40% ($p<0.05$) (FIG. 1b). Thirty minutes after the sympathetic nerve stimulation, the vasodilatation evoked by the stimulation of the parasympathetic nerve was still reduced by 28±5% (FIG. 6b). After one hour, the effects of parasympathetic stimulations were similar in magnitude to those before the sympathetic stimulation (FIG. 5b and 6b).

Figure 5C:
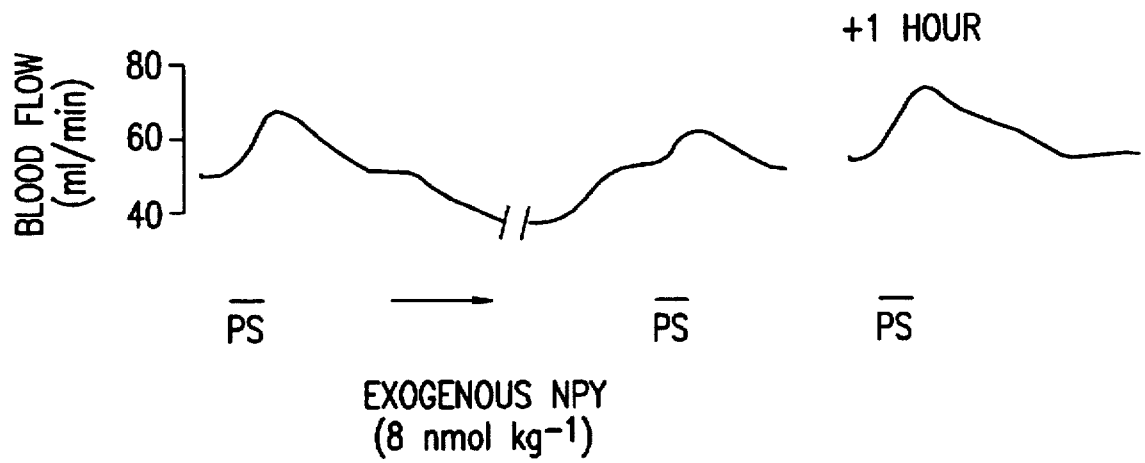

The administration of exogenous NPY (8 nmol $kg^{-1}$, i.v.) increased arterial blood pressure by 25±7 mmHg lasting 7.4±1.8 min. In parallel the blood flow in the internal maxillary artery was reduced by 43±8%. Atropine-resistant vasodilations evoked by parasympathetic stimulations at 20 and 30 Hz were reduced by approximately 45% ($p<0.05$) after the administration of exogenous NPY (FIG. 5c and 7). The vasodilatation induced by parasympathetic stimulations at 30 and 30 Hz remained significantly reduced ($p<0.05$) 30 min after the administration of exogenous NPY (FIG. 7). One hour after the completion of the NPY infusion, stimulation of the parasympathetic nerve evoked increases in nasal blood flow similar in magnetic to those before the NPY administration (FIG. 5c and 7).

Figures 8A, 8B:
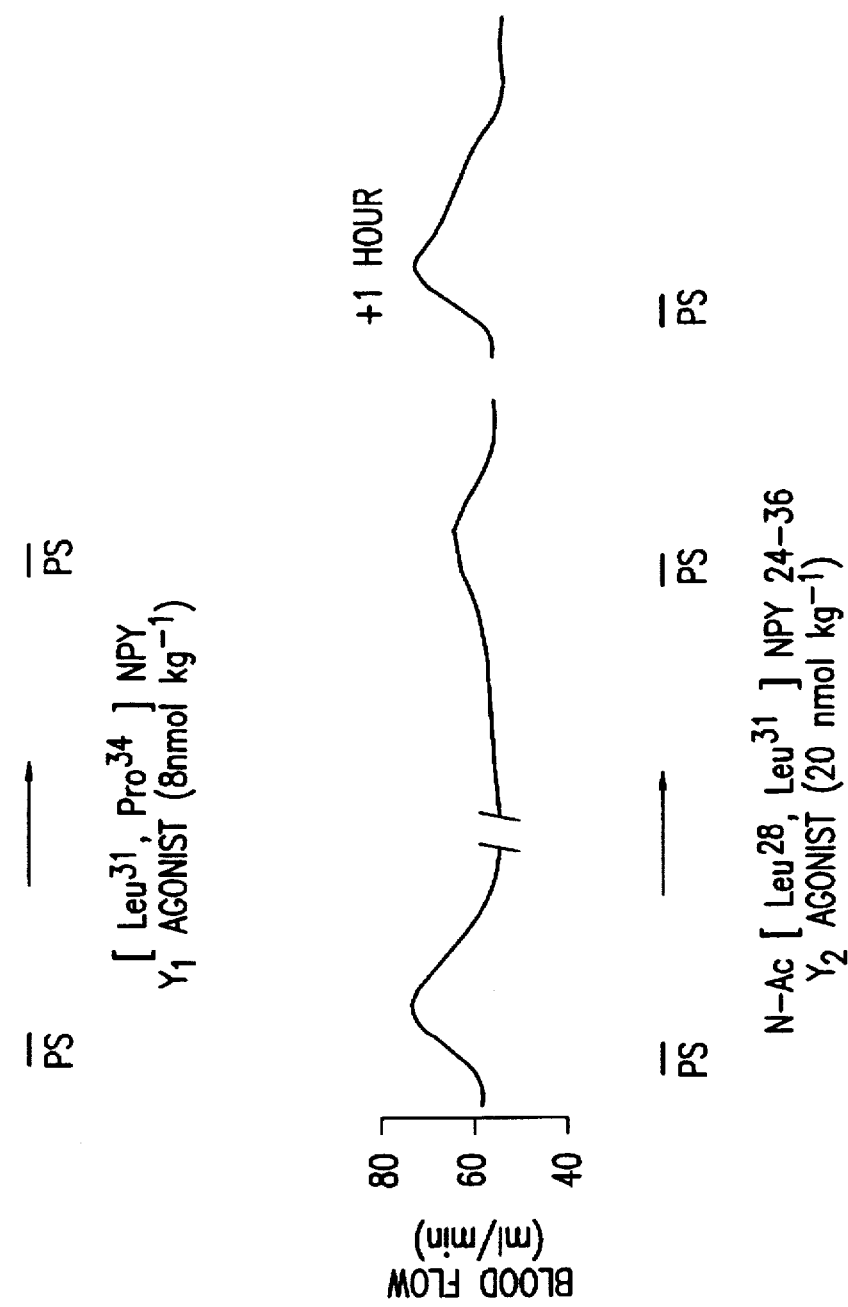

The injection of the putative $Y_1$ receptor agonist [$Leu^{31}$, $Pro^{34}$] NPY increased femoral blood/pressure by 23±2.8 mm Hg lasting more than 7 min (not shown), i.e. the same as NPY. In parallel, the nasal mucosa blood flow was reduced by an average 20% (FIG. 8a). The vasodilator responses to parasympathetic nerve stimulations were not modified after the administration of [$Leu^{31}$, $Pro^{31}$] NPY (FIG. 8a).

Both blood pressure and nasal blood flow remained unchanged after the infusion of the NPY analog N-acetyl [$Leu^{28}$, $Leu^{31}$] NPY 24–36 (FIG. 8b).

However the vasodilator responses to parasympathetic nerve stimulations at 10, 20 and 30 Hz were significantly reduced by an average 50% ($p<0.05$) after the administration of the Y2 receptor agonist (FIG. 8b). Thirty minutes later, the response to parasympathetic nerve stimulation remained significantly reduced by 31±5% (not shown). One hour after the infusion of the $Y_2$ receptor agonist, the vasodilatation evoked by the parasympathetic stimulations remained smaller but were not significantly different in magnitude to those obtained before the infusion of the $Y_2$ receptor agonist (FIG. 8b).

Local intra arterial injections of ACh, VIP and PHI evoked dose-dependant reductions of the Rma (FIG. 9) without significant modification of the arterial blood pressure. On a molar basis the rank order potency was ACh>VIP>PHI. Exogenous NA induced dose-dependant increases in Rma (not shown). The vasodilatory effect of ACh was rapid whereas those of VIP and PHI were slow in onset and long lasting (not shown). The effect of ACh and NA were abolished after pretreatment with the α-adrenoceptor blockers and atropine whereas the vasodilatory effect of VIP and PHI remained intact (not shown).

Discussion

The results of the present study show that sympathetic nerve stimulation attenuates subsequent parasympathetic nerve-evoked nasal vasodilatation in anaesthetised dogs. Similar interactions between sympathetic and parasympathetic system in the vascular control of the nasal mucosa have been recently described in cats (Lacroix et al., 1994).

In dogs in vivo, NPY released upon strong sympathetic nerve stimulation, inhibits ACh release from postganglionic parasympathetic nerve and reduces vagal effectiveness at the heart (Potter, 1985; Warner & Levy, 1989). Similar mechanisms may be involved in the inhibitory interactions which occur between sympathetic and parasympathetic nasal perivascular nerves during their activation. According to the observations reported here, it is likely that sympathetically released NPY attenuates non cholinergic vasodilatation in the dog nasal mucosa under control conditions.

The pre-ganglionic parasympathetic nature of the vidian nerve was confirmed by the inhibition of vasodilatation evoked by its electrical stimulation after administration of the ganglion blocker chlorisondamine (2 mg $kg^{-1}$, i.v.). Parasympathetic-evoked vasodilatation was not modified after pretreatment with adrenoceptor blockers and atropine, suggesting the involvement of non-adrenergic non-cholinergic mechanisms. As reported earlier by Malm et al. (1980), the atropine-resistant nasal vasodilatation evoked by stimulation of the vidian nerve could be mimicked by exogneous VIP and to a lesser extent by PHI. Since VIP is present in perivascular post-ganglionic parasympathetic neurons in the nasal mucosa (Uddman et al., 1981), this neuropeptide is most likely a mediator candidate for the non-adrenergic, non-cholinergic parasympathetic vasodilatation observed in the present study.

After the administration of both adrenergic and cholinergic antagonists, the attenuation of the parasympathetic vasodilatation remained intact, whereas the effect of both NA and ACh were abolished. The developed NPY analog. N-acetyl [$Leu^{28}$, $Leu^{31}$]NPY 24–36, has functional specificity for the prejunctional $Y_2$ receptor since it attenuates cardiac vagal action without a significant postjunctional $Y_1$-mediated pressor effect. In the present study, the attenuation of the atropine-resistant parasympathetic vasodilatation was mimicked by both NPY and the $Y_2$-receptor agonist N-acetyl [$Leu^{28}$, $Leu^{31}$], NPY 24–36. This new NPY analog has no pressor effects in dogs. In contrast, the $Y_1$-receptor agonist [$Leu^{31}$, $Pro^{34}$] NPY has shown similar vasopressor effects to exogneous NPY but has no influence on the parasympathetic nerve-evoked vasodilatation. Taken together, these observations strongly suggest that sympathetically released NPY has a prolonged inhibitory effect on parasympathetic vasodilatation via prejunctional $Y_2$ receptors.

In conclusion, the present observations show that sympathetic nerve stimulation and exogenous NPY have long lasting inhibitory effects on parasympathetic nerve-evoked vasodilatation in the dog nasal mucosa. These sympathetic-parasympathetic interactions could be mimicked by N-acetyl [$Leu^{28}$, $Leu^{31}$] NPY 24–36, a specific $Y_2$ receptor agonist.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

References

Aakerlund, L., U. Gether, T. W. Schwartz, and O. Thastrup, 1990, $Y_1$ receptors for neuropeptide Y are coupled to mobilization of intracellular calcium and inhibition of adenylate cyclase, FEBS Lett. 260, 73.

Bax, A. and D. G. Davis, 1985, MLEV-17-based two-dimensional homonuclear magnetization transfer spectroscopy. J. Magn. Res. 65, 355.

Berridge, T. L. & Roach A. G. (1986). Characterisation of α-adrenoceptors in the vasculature of the canine nasal mucosa. Br. J. Pharmacol., 88, 345–354.

Cohen, F. E., G. J., Strewler, M. Shannon Bradley, M. Carlquist, M. Nilsson, M. Ericsson, T. L. Ciardelli and T. A. Nissenson, 1991, Analogs of parathyroid hormone modified at positions 3 and 6. J. Biol. Chem. 266, 1997.

Dahlöff, C., P. Dahlöff and J. M. Lundberg, 1985, Enhancement of blood pressure increase upon α-adrenoceptor activation and direct pressor effects in pithed rats, Eur. J. Pharmacol. 109, 289.

Darbon, H., J.-M. Bernasson, C., Deleuze, J. Chen, A. Roussel and C. Cambillau, 1992, Solution conformation of human neuropeptide Y b1 1H nuclear magnetic resonance and restrained modular dynamics, Eur. J. Biochem. 209, 765.

Dill, A. 1986, in The Application of Electron Impact Mass Spectrometry in Structural Analysis of Peptides and Proteins: Practical Protein Chemistry chapter 2, (Darbre, A. ed) 528, John Wiley and Sons. N.Y.

Eccles, R. & Wilson, H. (1973). The parasympathetic secretory nerves of the nose of the cat. J. Physiol., 230, 213–223.

Edvinsson, L. 1988, The effects of neuropeptide Y on the circulation, ISI Atlas of Science: Pharmacology 2, 359.

Ferrin, T. E., C. C. Huan, L. E. Jarvis and R. Langridge, 1988, The MIDAS display system, J. Mol. Graphics 6, 13.

Fuhlendorff, J., U. Gether, L. Aakerlund, N. Langeland-Johansen, H. Tegerson, S. G. Melberg, U. B. Olsen, O. Thastrup, and T. W. Schwartz, 1990, [Leu[31], Pro[34]] Neuropeptide Y: A specific $Y_1$ receptor agonist, Proc. Natl. Acad. Sci. 87, 182.

Gardner, T. D. and E. K. Potter, 1988, Dependence of non-adrenergic inhibition of cardiac vagal action on peak frequency of sympathetic stimulation in the dog, J. Physiol. 405, 115.

Griesinger, C., G. Otting, K. Wüthrich and R. R. Ernst, 1988, Clean TOCSY for $^1$H spin system identification in macromolecules, J. Am. Chem. Soc. 110, 7870.

Grundemar, L., C. Wahlestedt, G. H. Shen, Z. Zukowska-Grojec and R. Hakanson, 1990a, Biphasic blood pressure response to neuropeptide Y in anaesthetised rats, Eur. J. Pharmacol. 179, 83.

Grundemar, L. and R. Hakanson, 1990b, Effects of various neuropeptideY/peptide YY fragments on electrically-evoked contractions of the rat vas deferens, Br. J. Pharmacol. 100, 190.

Grundemar, L. and R. Hakanson, 1991 Neuropeptide Y, peptide YY and C-terminal fragments release histamine from rat peritoneal mast cells, 1991, Br. J. Pharmacol. 104, 776.

Grundemar L., S. E. Jonas, N. Mörner, D. Högestätt. C. Wahlestedt and R. Hakanson, 1992, Characterization of vascular neuropeptide Y receptors. Br. J. Pharmacol. 105, 45.

Grundemar, L., J. L. Krstenansky and R. Hakanson, 1993, Activation of neuropeptide $Y_1$ and $Y_2$ receptors by substituted and truncated neuropeptide Y analogs: identification of signal epitopes. Eur. J. Pharmacol. 232, 271.

Grynkiewicsz, G., M. Poonie, and R. Y. Tsien, 1985, A new generation of $Ca^{2+}$ indicators with greatly improved fluorescence properties, J. Biol. Chem. 260, 3440.

Güntert, P., W. Braun, and K. Wüthrich, 1991, Efficient computation of three dimensional protein structures in solution from magnetic resonance data using the program DIANA and the supporting programs CALIBA, HABAS and GLOMSA, J. Mol. Biol. 217, 517.

Herzog, H., Y. J. Hort, H. J. Ball, G. Hayes, J. Shine, and L. A. Selbie, 1992, Cloned human neuropeptide Y receptor couples to two different second messenger systems, Proc. Natl. Acad. Sci. U.S.A. 89, 5794.

Jeener, J., B. H. Meiser, P. Buchmann and R. R. Ernst, 1979, Investigation of exchange processes by two-dimensional NMR spectroscopy, J. Chem. Phys. 71, 4546.

Lacroix, J. S., Stjarne, P., Anggard, A. & Lundberg, J. M. (1988). Sympathetic vascular control of the pig nasal mucosa (1): Increased resistance and capacitance vessels responses upon stimulation with irregular bursts compared to continuous impulses. Acta Physiol. Scand., 132, 83–90.

Lundberg, J. M., Anggard, A., Emson, P., Fahrenkrug, J. & Hokfelt, T. (1981). Vasoactive intestinal polypeptide and cholinergic mechanisms in cat nasal mucosa: Studies on choline acetyltransferase and release of vasoactive intestinal polypeptide. Proc. Natl. Acad Sci. U.S.A., 78, 5255–5259.

Lundberg, J. M., A. Hemsen, O. Larsson, A. Rudehill, A. Saria, and B. A. Fredholm, 1988, Neuropeptide Y receptor in pig spleen: binding characteristics, reduction of cyclic AMP formation and calcium antagonist inhibition of vasoconstriction, Eur. J. Pharmacol. 145, 21.

Macura, S., Y. Huang, D. Sutter, and R. R. Ernst, 1981, Two-dimensional chemical exchange and cross-relaxation spectroscopy of coupled nuclear spins, J. Magn. Reson. 43, 259.

Neugerbauer, W., W. K. Surewicz, H. L. Gordon, R. L. Somorjai, W. Sung and G. E. Willick, 1992, Structural elements of human parathyroid hormone and their possible relation to biological activities, Biochemistry 31, 2056.

Potter, E. K., 1985, Prolonged non-adrenergic inhibition of cardiac vagal action following sympathetic stimulation: neuromodulation by neuropeptide Y? Neurosci. lett. 54, 117.

Potter, E. K., 1988, Neuropeptide Y as an autonomic neurotransmitter, Pharm. Ther., 37, 251.

Potter, E. K., L. Mitchell, M. J. D. McCloskey, A. Tseng, A. E. Goodman, J. Shine and D. I. McCloskey, 1989, Pre- and postjunctional actions of neuropeptide Y and related peptides, Regul. Pept. 25, 167.

Potter, e. K., J. Fuhlendorff and T. W. Schwartz, 1991, [Pro[34]] neuropeptide Y selectively identifies postjunctional-mediated actions of neuropeptide Y in vivo in rats and dogs, Eur. J. Pharmacol. 193, 15.

Potter, E. K. and M. J. D. McCloskey, 1992, [Leu[31], Leu[34]] neuropeptide Y, a selective functional postjunctional agonist at neuropeptide Y receptors in anaesthetised rats, Neurosci. Lett. 134, 183.

Potter, E. K., L. Edvinsson and T. Gustafsson, 1992, Antagonism of pre- and postjunctional responses to neuropeptide Y and sympathetic stimulation by D-myoinositol-1,2,6-trisphosphate in the anaesthetised dog, Eur. J. Pharmacol. 221, 307.

Potter, E. K., Tseng, A., Inglis, A., Selbie, L. A., Moriarty, M., McCloskey M. & Shine, J. (1993). A molecule with selective postjunctional NPY antagonist effects, and another with selective prejunctional NPY-like agonist effects. Proceedings of the NPY meeting, Cambridge, B34.

Revington, M. L., E. K. Potter and D. I. McCloskey, 1987, Effects of neuropeptide Y on the pressor responses to phenylephine and to activation of the sympathetic nervous system in anaesthetised rats, Clin. Esp. Pharmacol, Physiol. 14, 703.

Rioux, F., H. Bachelard, J. C. Martel and S. St.-Piere, 1986, The vasoconstrictor effect of neuropeptide Y and related peptides in the guinea pig isolated heart, Peptides 7, 27.

Sambrook, J., E. F. Fritsch and T. Maniatis, 1989, Molecular cloning: a laboratory manual. Cold Spring Harbor Lab., Cold Spring Harbor, N.Y. p16.

Sargent, D. F. and R. Schwyzer, 1986, Membrane lipid phase as catalyst for peptide-receptor interactions, Proc. Natl. Acad. Sci. USA 83, 5774.

Schartz, T. W., J. Fuhlendorff, H., Langeland, J. C. Togerson, S. P. Sheikh, 1989, in Neuropeptide Y—XIV Nobel Symposium, ed: V. Mutt., T. Hökfelt, K. Fuxe and J. M. Lundberg, Raven, N.Y. pp143.

Sheikh, S. P., R. Håkanson and T. W. Schwartz, 1989, $Y_1$ and $Y_2$ receptors for neuropeptide Y, FEBS Lett. 245, 209.

Shen, G. H., L. Grundemar, Z. Zukowska-Grojec, R. Hakanson and C. Wahlestedt, 1991, C-terminal neuropeptide Y fragments are mast cell-dependent vasodepressor agents, Eur. J. Pharmacol, 204, 249.

Tatemoto, K., M. Carlquist and V. Mutt, 1982, Neuropeptide Y—A novel brain peptide with structural similarities to peptide YY and pancreatic polypeptide, Nature 296, 659.

Uddman, R., Alumets, J., Densert, O., Hakansson, R. & Sundler, F. (1978). Occurrence and distribution of VIP nerves in the nasal mucosa and tracheobronchial wall. Acta Otolaryngol. (Stockholm), 85, 443–448.

Wahelstedt, C., N. Yanaihara and R. Håkanson, 1986, Evidence for different pre- and post-junctional receptors for neuropeptide Y and related peptides, Regul. Pep. 10, 243.

Warner, M. R. and M. N. Levy, 1989, Neuropeptide Y as a putative modulator of the vagal effects on heart rate, Cir. Res. 64, 882.

Wüthrich, K., 1986, NMR of Proteins and Nucleic Acids, J. Wiley and Sons, New York.

Zar, J. H., 1984, Biostatistical Analysis, 2nd edn, Prentice-Hall, Englewood Cliffs, N.J.

Zuiderweg, E. R. P., K. Hallenga and E. T. Olejniczak, 1986, Improvement of 2D NOE spectra of biomacromolecules in $H_2O$ solution by coherent suppression of the solvent resonance, J. Magn. Reson. 70, 336.

We claim:

1. A method of treating nasal congestion which comprises administering to a person in need of such treatment an effective amount of a composition comprising a peptide having the formula $X1(-X2-X3-X4-X5-X6-X7-X8-X9-X10-X11-X12-X13-X14)_N-X15$ wherein X1 is NH, $CH_3CO$ or one or two naturally occurring amino acids X2 is Leu, Ile or Val.

X3 is Arg, Lys or His,

X4 is His, Lys or Arg,

X5 is Tyr or Phe,

X6 is Leu, Ile or Val,

X7 is Asn or Gln,

X8 is Leu, Ile or Val,

X9 is Leu, Ile or Val,

X10 is Thr or Ser,

X11 is Arg, His or Lys,

X12 is Gln or Asn,

X13 is Arg, His or Lys,

X14 is Tyr or Phe,

X15 is COOH, $NH_2$ or one or two naturally occurring amino acids with the terminal amino acid being in the normal or carboxamide form; and n is 1 to 5.

2. A method in accordance with claim 1 wherein the composition comprises the peptide $CH_3CO$-Leu-Arg-His-Tyr-Leu-Asn-Leu-Leu-Thr-Arg-Gln-Arg-Tyr-$NH_2$ or $CH_3CO$-Leu-Arg-His-Tyr-Ile-Asn-Leu-Ile-Thr-Arg-Gln-Arg-Tyr-$NH_2$ or $NH_2$-Leu-Arg-His-Tyr-Leu-Asn-Leu-Leu-Thr-Arg-Gln-Arg-Tyr-$NH_2$ or $NH_2$-Leu-Arg-His-Tyr-Ile-Asn-Leu-Ile-Thr-Arg-Gln-Arg-Tyr-$NH_2$.

3. A method in accordance with claim 1 wherein the composition comprises $CH_3CO$-Leu-Arg-His-Tyr-Leu-Asn-Leu-Leu-Thr-Arg-Gln-Arg-Tyr-$NH_2$.

4. A method as claimed in claim 1 in which the composition is administered as a nasal spray.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 15 amino acids
        ( B ) TYPE: amino acid
        ( C ) STRANDEDNESS: Not Relevant
        ( D ) TOPOLOGY: linear ( i i ) MOLECULE TYPE: peptide ( v ) FRAGMENT TYPE: N-terminal ( i x ) FEATURE:
        ( A ) NAME/KEY: Modified-site
        ( B ) LOCATION: 1..2
        ( D ) OTHER INFORMATION: /label=X1
            / note= "X1 is NH, CH3CO or one or two naturally occurring amino acids"

( i x ) FEATURE:
        ( A ) NAME/KEY: Modified-site
        ( B ) LOCATION: 2..3
        ( D ) OTHER INFORMATION: /label=X2
            / note= "X2 is Leu, Ile or Val"

( i x ) FEATURE:
        ( A ) NAME/KEY: Modified-site
        ( B ) LOCATION: 3..4
        ( D ) OTHER INFORMATION: /label=X3
            / note= "X3 is Arg, Lys or His"

( i x ) FEATURE:
        ( A ) NAME/KEY: Modified-site
        ( B ) LOCATION: 4..5
        ( D ) OTHER INFORMATION: /label=X4
            / note= "X4 is His, Lys or Arg"

( i x ) FEATURE:
        ( A ) NAME/KEY: Modified-site
        ( B ) LOCATION: 5..6
        ( D ) OTHER INFORMATION: /label=X5
            / note= "X5 is Tyr or Phe"

(ix) FEATURE:
    (A) NAME/KEY: Modified-site
    (B) LOCATION: 6..7
    (D) OTHER INFORMATION: /label=X6
        / note= "X6 is Leu, Ile or Val"

(ix) FEATURE:
    (A) NAME/KEY: Modified-site
    (B) LOCATION: 7..8
    (D) OTHER INFORMATION: /label=X7
        / note= "X7 is Asn or Gln"

(ix) FEATURE:
    (A) NAME/KEY: Modified-site
    (B) LOCATION: 8..9
    (D) OTHER INFORMATION: /label=X8
        / note= "X8 is Leu, Ile or Val"

(ix) FEATURE:
    (A) NAME/KEY: Modified-site
    (B) LOCATION: 9..10
    (D) OTHER INFORMATION: /label=X9
        / note= "X9 is Leu, Ile or Val"

(ix) FEATURE:
    (A) NAME/KEY: Modified-site
    (B) LOCATION: 10..11
    (D) OTHER INFORMATION: /label=X10
        / note= "X10 is Thr or Ser"

(ix) FEATURE:
    (A) NAME/KEY: Modified-site
    (B) LOCATION: 11..12
    (D) OTHER INFORMATION: /label=X11
        / note= "X11 is Arg, His or Lys"

(ix) FEATURE:
    (A) NAME/KEY: Modified-site
    (B) LOCATION: 12..13
    (D) OTHER INFORMATION: /label=X12
        / note= "X12 is Gln or Asn"

(ix) FEATURE:
    (A) NAME/KEY: Modified-site
    (B) LOCATION: 13..14
    (D) OTHER INFORMATION: /label=X13
        / note= "X13 is Arg, His or Lys"

(ix) FEATURE:
    (A) NAME/KEY: Modified-site
    (B) LOCATION: 14..15
    (D) OTHER INFORMATION: /label=X14
        / note= "X14 is Tyr or Phe. The peptide
        (X2 - X3 - X4 - X5 - X6 - X7 - X8 - X9 - X10 - X11 - X12 - X13 - X14) may be
        repeated n times, where n is 1 to 5."

(ix) FEATURE:
    (A) NAME/KEY: Modified-site
    (B) LOCATION: 14..15
    (D) OTHER INFORMATION: /label=X15
        / note= "X15 is COOH, NH2 or one or two naturally
        occurring amino acids with the terminal amino acid
        being in the normal or carboxamide form."

(xi) SEQUENCE DESCRIPTION: SEQ ID NO:1:

```
Xaa Xaa Xaa Xaa Xaa Xaa Xaa Xaa Xaa Xaa Xaa Xaa Xaa Xaa Xaa
 1               5                  10                  15
```

(2) INFORMATION FOR SEQ ID NO:2:

(i) SEQUENCE CHARACTERISTICS:
        (A) LENGTH: 13 amino acids
        (B) TYPE: amino acid
        (C) STRANDEDNESS: Not Relevant
        (D) TOPOLOGY: linear (ii) MOLECULE TYPE: peptide (v) FRAGMENT TYPE: N-terminal (ix) FEATURE:
  (A) NAME/KEY: Modified-site
  (B) LOCATION: 1..2
  (D) OTHER INFORMATION: /product="Group X1 at NH2
        terminus"
        / label= X1
        / note= "X1 is CH3CO"

(ix) FEATURE:
  (A) NAME/KEY: Modified-site
  (B) LOCATION: 12..13
  (D) OTHER INFORMATION: /product="Group X14 at COOH
        terminus"
        / label= X14
        / note= "X14 is NH2"

(xi) SEQUENCE DESCRIPTION: SEQ ID NO:2:

```
Leu Arg His Tyr Leu Asn Leu Leu Thr Arg Gln Arg Tyr
1               5                   10
```

(2) INFORMATION FOR SEQ ID NO:3:

(i) SEQUENCE CHARACTERISTICS:
    (A) LENGTH: 13 amino acids
    (B) TYPE: amino acid
    (C) STRANDEDNESS: Not Relevant
    (D) TOPOLOGY: linear (ii) MOLECULE TYPE: peptide (v) FRAGMENT TYPE: N-terminal (ix) FEATURE:
    (A) NAME/KEY: Modified-site
    (B) LOCATION: 1..2
    (D) OTHER INFORMATION: /product="Group X1 at NH2
          terminus"
          / label= X1
          / note= "X1 is CH3CO"

(ix) FEATURE:
    (A) NAME/KEY: Modified-site
    (B) LOCATION: 12..13
    (D) OTHER INFORMATION: /product="Group X14 at COOH
          terminus"
          / label= X14
          / note= "X14 is NH2"

(xi) SEQUENCE DESCRIPTION: SEQ ID NO:3:

```
Leu Arg His Tyr Ile Asn Leu Leu Thr Arg Gln Arg Tyr
1               5                   10
```

(2) INFORMATION FOR SEQ ID NO:4:

(i) SEQUENCE CHARACTERISTICS:
    (A) LENGTH: 13 amino acids
    (B) TYPE: amino acid
    (C) STRANDEDNESS: Not Relevant
    (D) TOPOLOGY: linear (ii) MOLECULE TYPE: peptide (v) FRAGMENT TYPE: N-terminal (ix) FEATURE:
    (A) NAME/KEY: Modified-site
    (B) LOCATION: 1..2
    (D) OTHER INFORMATION: /product="Group X1 at NH2
          terminus"
          / label= X1
          / note= "X1 is NH2"

(ix) FEATURE:

```
            ( A ) NAME/KEY: Modified-site
            ( B ) LOCATION: 12..13
            ( D ) OTHER INFORMATION: /product="Group X14 at COOH
                    terminus"
                    / label= X14
                    / note= "X14 is CH3CO"

( x i ) SEQUENCE DESCRIPTION: SEQ ID NO:4:

Leu  Arg  His  Tyr  Leu  Asn  Leu  Leu  Thr  Arg  Gln  Arg  Tyr
 1              5                        10

( 2 ) INFORMATION FOR SEQ ID NO:5:

( i ) SEQUENCE CHARACTERISTICS:
                ( A ) LENGTH: 13 amino acids
                ( B ) TYPE: amino acid
                ( C ) STRANDEDNESS: Not Relevant
                ( D ) TOPOLOGY: linear ( i i ) MOLECULE TYPE: peptide ( v ) FRAGMENT TYPE: N-terminal ( i x ) FEATURE:
                ( A ) NAME/KEY: Modified-site
                ( B ) LOCATION: 1..2
                ( D ) OTHER INFORMATION: /product="Group X1 at NH2
                        terminus"
                        / label= X1
                        / note= "X1 is NH2"

( i x ) FEATURE:
                ( A ) NAME/KEY: Modified-site
                ( B ) LOCATION: 12..13
                ( D ) OTHER INFORMATION: /product="Group X14 at COOH
                        terminus"
                        / label= X14
                        / note= "X14 is CH3CO"

( x i ) SEQUENCE DESCRIPTION: SEQ ID NO:5:

Leu  Arg  His  Tyr  Ile  Asn  Leu  Leu  Thr  Arg  Gln  Arg  Tyr
 1              5                        10
```